United States Patent
Kinrot et al.

(10) Patent No.: US 9,307,918 B2
(45) Date of Patent: Apr. 12, 2016

(54) DEVICES AND METHODS FOR MONITORING CEREBRAL HEMODYNAMIC CONDITIONS

(75) Inventors: Opher Kinrot, Racnana (IL); Shlomi Ben-Ari, Benyamina (IL)

(73) Assignee: Orsan Medical Technologies Ltd., Netania (IL)

( * ) Notice: Subject to any disclaimer, the term of this patent is extended or adjusted under 35 U.S.C. 154(b) by 1113 days.

(21) Appl. No.: 13/252,191

(22) Filed: Oct. 3, 2011

(65) Prior Publication Data

US 2012/0203134 A1  Aug. 9, 2012

Related U.S. Application Data

(60) Provisional application No. 61/441,248, filed on Feb. 9, 2011, provisional application No. 61/474,739, filed on Apr. 12, 2011.

(51) Int. Cl.
| | |
|---|---|
| *A61B 5/0265* | (2006.01) |
| *A61B 5/0295* | (2006.01) |
| *A61B 5/053* | (2006.01) |
| *A61B 5/00* | (2006.01) |

(52) U.S. Cl.
CPC ............ *A61B 5/0265* (2013.01); *A61B 5/0295* (2013.01); *A61B 5/053* (2013.01); *A61B 5/4064* (2013.01); *A61B 5/6803* (2013.01)

(58) Field of Classification Search
CPC .... A61B 5/0295; A61B 5/053; A61B 5/0531; A61B 5/0535; A61B 5/0537
USPC ........................................................ 600/547
See application file for complete search history.

(56) References Cited

U.S. PATENT DOCUMENTS

| | | | |
|---|---|---|---|
| 3,835,839 A | 9/1974 | Brown | |
| 3,851,641 A | 12/1974 | Toole et al. | |
| 3,871,359 A | 3/1975 | Pacela | |
| 3,994,284 A | 11/1976 | Voelker | |

(Continued)

FOREIGN PATENT DOCUMENTS

| | | |
|---|---|---|
| CN | 1044899 A | 8/1990 |
| CN | 1062649 A | 7/1992 |

(Continued)

OTHER PUBLICATIONS

Abboud, S. et al. (Jan. 1996) "Left-Right Asymmetry of Visual Evoked Potentials in Brain-Damaged Patients: A Mathematical Model and Experimental Results" *Annals of Biomedical Engineering*, 24(1):75-86.

(Continued)

*Primary Examiner* — Rene Towa
(74) *Attorney, Agent, or Firm* — Finnegan, Henderson, Farabow, Garrett & Dunner, LLP

(57) ABSTRACT

Devices, and methods for monitoring cerebro-hemodynamic signals are disclosed. In one aspect, the devices and methods may include receiving at least one signal characterizing a bioimpedance measurement. The at least one signal may be correlated with the timing of a cardiac wave and analyzed to ascertain an extent of an expected characteristic within the signal. The extent of the expected characteristic may be used to provide information for predicting a physiological brain condition. The at least one signal may include two signals, obtained from opposite brain hemispheres, and may be a bioimpedance signal.

28 Claims, 10 Drawing Sheets

(56) References Cited

U.S. PATENT DOCUMENTS

| | | | |
|---|---|---|---|
| 4,308,873 A | 1/1982 | Maynard | |
| 4,417,581 A | 11/1983 | Dawson | |
| 4,442,845 A | 4/1984 | Stephens | |
| 4,649,932 A | 3/1987 | Smith | |
| 4,676,253 A | 6/1987 | Newman et al. | |
| 4,905,705 A | 3/1990 | Kizakevich et al. | |
| 4,984,567 A | 1/1991 | Kageyama et al. | |
| 5,040,540 A | 8/1991 | Sackner | |
| 5,068,619 A | 11/1991 | Nakano et al. | |
| 5,265,615 A | 11/1993 | Frank et al. | |
| 5,282,840 A | 2/1994 | Hudrlik | |
| 5,315,512 A | 5/1994 | Roth | |
| 5,353,802 A | 10/1994 | Ollmar et al. | |
| 5,396,893 A | 3/1995 | Oberg et al. | |
| 5,429,131 A | 7/1995 | Scheinman et al. | |
| 5,584,297 A | 12/1996 | Bodóet et al. | |
| 5,617,873 A | 4/1997 | Yost et al. | |
| 5,676,145 A | 10/1997 | Bar-Lavie | |
| 5,694,939 A | 12/1997 | Cowings | |
| 5,746,214 A | 5/1998 | Brown et al. | |
| 5,749,369 A | 5/1998 | Rabinovich et al. | |
| 5,788,643 A | 8/1998 | Feldman | |
| 5,807,270 A | 9/1998 | Williams | |
| 5,865,757 A | 2/1999 | Hoeft | |
| 6,014,583 A | 1/2000 | Nakagawara et al. | |
| 6,022,322 A | 2/2000 | Prutchi | |
| 6,081,743 A | 6/2000 | Carter et al. | |
| 6,091,977 A | 7/2000 | Tarjan et al. | |
| 6,117,089 A | 9/2000 | Sinha | |
| 6,169,914 B1 | 1/2001 | Hovland et al. | |
| 6,214,019 B1 | 4/2001 | Manwaring et al. | |
| 6,223,069 B1 | 4/2001 | Pfeiffer et al. | |
| 6,245,027 B1 | 6/2001 | Alperin | |
| 6,413,223 B1 | 7/2002 | Yang et al. | |
| 6,491,647 B1 | 12/2002 | Bridger et al. | |
| 6,511,437 B1 | 1/2003 | Nakamura et al. | |
| 6,640,121 B1 | 10/2003 | Telischi et al. | |
| 6,718,196 B1 | 4/2004 | Mah et al. | |
| 6,773,407 B2 | 8/2004 | Yost et al. | |
| 6,819,950 B2 | 11/2004 | Mills | |
| 6,832,113 B2 | 12/2004 | Belalcazar | |
| 6,875,176 B2 | 4/2005 | Mourad et al. | |
| 6,976,963 B2 | 12/2005 | Clift | |
| 6,996,428 B2 | 2/2006 | Kislov et al. | |
| 7,024,238 B2 | 4/2006 | Bergethon | |
| 7,041,063 B2 | 5/2006 | Abreu | |
| 7,998,080 B2 | 8/2011 | Ben-Ari et al. | |
| 8,109,880 B1 | 2/2012 | Pranevicius et al. | |
| 8,211,031 B2 | 7/2012 | Poupko et al. | |
| 8,366,627 B2 | 2/2013 | Kashif et al. | |
| 8,702,615 B2 | 4/2014 | Shapira et al. | |
| 2002/0161292 A1 | 10/2002 | Wintermark et al. | |
| 2002/0188206 A1 | 12/2002 | Davis et al. | |
| 2003/0144719 A1 | 7/2003 | Zeijlemaker et al. | |
| 2003/0167012 A1 | 9/2003 | Friedman et al. | |
| 2003/0191410 A1 | 10/2003 | Yost et al. | |
| 2004/0010185 A1 | 1/2004 | Kimball et al. | |
| 2004/0030258 A1 | 2/2004 | Williams et al. | |
| 2004/0034294 A1 | 2/2004 | Kimball et al. | |
| 2004/0049105 A1 | 3/2004 | Crutchfield et al. | |
| 2004/0267153 A1 | 12/2004 | Bergethon | |
| 2005/0054939 A1 | 3/2005 | Ben-Ari et al. | |
| 2005/0090753 A1 | 4/2005 | Goor et al. | |
| 2005/0107719 A1 | 5/2005 | Arad (Abbound) | |
| 2005/0192488 A1 | 9/2005 | Bryenton et al. | |
| 2006/0047201 A1 | 3/2006 | Eide | |
| 2006/0094964 A1 | 5/2006 | Ragauskas et al. | |
| 2006/0122523 A1 | 6/2006 | Bonmassar et al. | |
| 2006/0149139 A1 | 7/2006 | Bonmassar et al. | |
| 2006/0189883 A1 | 8/2006 | Pomfrett et al. | |
| 2006/0200033 A1 | 9/2006 | Keren et al. | |
| 2007/0225585 A1 | 9/2007 | Washbon et al. | |
| 2007/0273504 A1 | 11/2007 | Tran | |
| 2007/0287899 A1* | 12/2007 | Poupko et al. ............ 600/383 |
| 2007/0287923 A1 | 12/2007 | Adkins et al. | |
| 2008/0004904 A1 | 1/2008 | Tran | |
| 2008/0021332 A1* | 1/2008 | Brainard, III ............ 600/483 |
| 2008/0200787 A1 | 8/2008 | Shapira et al. | |
| 2008/0275352 A1 | 11/2008 | Shapira et al. | |
| 2009/0069647 A1 | 3/2009 | McNames et al. | |
| 2009/0088619 A1 | 4/2009 | Turner et al. | |
| 2009/0143656 A1 | 6/2009 | Manwaring et al. | |
| 2009/0149933 A1 | 6/2009 | Ameri | |
| 2009/0227881 A1* | 9/2009 | Reichman et al. ............ 600/506 |
| 2010/0063405 A1 | 3/2010 | Kashif et al. | |
| 2010/0069765 A1 | 3/2010 | Keren | |
| 2010/0204589 A1 | 8/2010 | Swoboda et al. | |
| 2010/0268096 A1 | 10/2010 | Berka et al. | |
| 2011/0130675 A1 | 6/2011 | Bibian et al. | |
| 2011/0196245 A1 | 8/2011 | Poupko et al. | |
| 2011/0201950 A1 | 8/2011 | Poupko et al. | |
| 2011/0251503 A1 | 10/2011 | Ben-Ari et al. | |
| 2012/0022349 A1 | 1/2012 | Poupko et al. | |
| 2012/0203091 A1 | 8/2012 | Kinrot et al. | |
| 2012/0203121 A1 | 8/2012 | Kinrot et al. | |
| 2012/0203122 A1 | 8/2012 | Kinrot et al. | |
| 2013/0041271 A1 | 2/2013 | Ben-Ari et al. | |
| 2013/0109979 A1 | 5/2013 | Poupko et al. | |
| 2013/0274615 A1 | 10/2013 | Ben-Ari et al. | |
| 2014/0163404 A1 | 6/2014 | Reichman et al. | |
| 2014/0358016 A1 | 12/2014 | Shapira et al. | |
| 2014/0371545 A1 | 12/2014 | Ben-Ari et al. | |

FOREIGN PATENT DOCUMENTS

| | | |
|---|---|---|
| CN | 1356090 A | 7/2002 |
| CN | 1806760 A | 7/2006 |
| CN | 101313844 A | 12/2008 |
| DE | 10061189 A1 | 6/2002 |
| EP | 0314088 B1 | 8/1995 |
| EP | 1057498 A2 | 12/2000 |
| EP | 1961376 A2 | 8/2008 |
| GB | 1538695 A | 1/1979 |
| JP | 01-113645 A | 5/1989 |
| JP | 03-118038 A | 5/1991 |
| JP | 05-43377 B2 | 7/1993 |
| JP | 06-078888 A | 3/1994 |
| JP | 07-000369 A | 1/1995 |
| JP | 2000-325324 A | 11/2000 |
| JP | 2001-104274 A | 4/2001 |
| JP | 2001-286452 A | 10/2001 |
| JP | 2002-010986 A | 1/2002 |
| JP | 2004-129809 A | 4/2004 |
| JP | 2004-321211 A | 11/2004 |
| RU | 2141249 C1 | 11/1999 |
| RU | 2163090 C1 | 2/2001 |
| RU | 2185091 C1 | 7/2002 |
| WO | WO 80/00913 A1 | 5/1980 |
| WO | WO 95/28126 A1 | 10/1995 |
| WO | WO 96/16692 A1 | 6/1996 |
| WO | WO 99/52426 A1 | 10/1999 |
| WO | WO 00/68647 A2 | 11/2000 |
| WO | WO 02/071923 A2 | 9/2002 |
| WO | WO 02/086530 A1 | 10/2002 |
| WO | WO 02/087410 A2 | 11/2002 |
| WO | WO 03/017834 A1 | 3/2003 |
| WO | WO 03/037181 A2 | 5/2003 |
| WO | WO 03/059164 A2 | 7/2003 |
| WO | WO 2004/054429 A2 | 7/2004 |
| WO | WO 2005/009204 A2 | 2/2005 |
| WO | WO 2006/006143 A1 | 1/2006 |
| WO | WO 2006/009771 A1 | 1/2006 |
| WO | WO 2006/011128 A1 | 2/2006 |
| WO | WO 2006/087696 A2 | 8/2006 |
| WO | WO 2006/121469 A1 | 11/2006 |
| WO | WO 2006/134501 A1 | 12/2006 |
| WO | WO 2007/036586 A2 | 4/2007 |
| WO | WO 2007/047966 A2 | 4/2007 |
| WO | WO 2008/072223 A1 | 6/2008 |
| WO | WO 2008/095059 A1 | 8/2008 |
| WO | WO 2009/072023 A1 | 6/2009 |
| WO | WO 2010/041204 A2 | 4/2010 |
| WO | WO 2010/041205 A2 | 4/2010 |

(56) References Cited

FOREIGN PATENT DOCUMENTS

| WO | WO 2010/041206 A1 | 4/2010 |
|----|-------------------|--------|
| WO | WO 2010/129026 A2 | 11/2010 |
| WO | WO 2012/140510 A2 | 10/2012 |

OTHER PUBLICATIONS

Albers, G.W. et al. (2004) "Antithrombotic and thrombolytic therapy for ischemic stroke." The Seventh ACCP Conference on Antithrombotic and Thrombolytic Therapy. *Chest*, 126(3 Suppl.):483S-512S.
Alperin et al. (2006) "From Cerebrospinal Fluid Pulsation to Noninvasive Intracranial Compliance and Pressure Measured by MRI Flow Studies" *Current Medical Imaging Reviews*, 2:117-129.
Baird et al. (Mar. 1999) "Asymmetries of cerebral perfusion in a stroke-age population" *J. Clin. Neurosci.*, 6(2):113-120.
Barbosa-Silva, M.C.G.et al. (2005) "Bioelectrical Impedance Analysis: Population Reference Values for Phase Angle by Age and Sex" *Am. J. Clin. Nutr.*, 82:49-52.
Bartocci, M. et al. (1999) "Cerebral Blood-Flow Monitor for Use in Neonatal Intensive Care Units" *Computer Methods and Programs in Biomedicine*, 59:61-73.
Baumgartner, C. et al. (Sep. 2005) "Functional Cluster Analysis of CT Perfusion Maps: A New Tool for Diagnosis of Acute Stroke?" *J. Digital Imaging*, 18(3):219-226.
Bellner, J. et al. (Jul. 2004) "Transcranial Doppler Sonography Pulsatility Index (PI) Reflects Intracranial Pressure (ICP)" *Surgical Neurology*, 62(1):45-51.
Bodo, M. et al. (1986) "Rheoencephalographic Changes During Increased Intracranial Pressure" in: Krieglstein, J. (ed): *Pharmacology of Cerebral Ischemia*. Elsevier, Amsterdam, 1986; pp. 265-269.
Bonmassar, G. and S. Iwaki (2004) "The Shape of Electrical Impedance Spectroscopy (EIS) Is Altered in Stroke Patients" *Proceedings of the 26th Annual International Conference of the IEEE EMBS*, San Francisco, CA, USA, Sep. 1-5, 2004, p. 3443-3446.
Braunfels, S. et al. (1997) "A Randomized, Controlled Trial of the Efficacy of Closed Chest Compressions in Ambulances" *Prehosp. Emrg. Care*, 1(3):128-131 (Abstract).
Colditz, P.B. et al. (1990) "Continuous Cerebral Electrical Impedance Monitoring in Sick Preterm Infants" Eur. J. Pediatr., 149:428-431.
Cornish, B.H. et al. (Mar. 1996) "Evaluation of multiple frequency bioelectrical impedance and Cole-Cole analysis for the assessment of body water volumes in healthy humans" *Eur. J. Clin. Nutr.*, 50(3):159-164.
Costloe, K. et al. (Mar. 1984) "A Comparison Between Electrical Impedance and Strain Gauge Plethysmography for the Study of Cerebral Blood Flow in the Newborn" *Pediatric Research*, 18(3):290-295.
Czosnyka, M. et al. (1998) "Cerebral Perfusion in Head-Injured Patients: A Noninvasive Assessment Using Transcranial Doppler Ultrasonography" *J. Neurosurg.*, 88:802-808.
Fugishima, M. et al. (1981) "Changes in local cerebral blood flow following bilateral carotid occlusion in spontaneously hypertensive and normotensive rats" *Stroke*, 12(6):874-876.
González, C. and B. Rubinsky et al. (2006) "A Theoretical Study on Magnetic Induction Frequency Dependence of Phase Shift in Oedema and Haematoma" *Physiol. Meas.*, 27:829-838.
Grönlund, J. et al. (1992) "High Frequency Variability of Transcephalic Electrical Impedance—A New Parameter for Monitoring of Neonatal Cerebral Circulation?" *Engineering in Medicine and Biology Society, 14th Annual International Conference of the IEEE*, vol. 6, pp. 2513-2515.
Grönlund, J. et al. (1997) "Transcephalic Electrical Impedance Provides a Means for Quantifying Pulsatile Cerebral Blood Volume Changes Following Head-Up Tilt" *Early Human Development*, 47:11-18.
Hagiwara, H. et al. (2008) "Predicting the Fate of Acute Ischemic Lesions Using Perfusion Computed Tomography" *J. Comput. Assist. Tomogr.*, 32:645-650.
Hoeffner, E.G. et al. (2004) "Cerebral Perfusion CT: Technique and Clinical Applications" *Radiology*, 231:632-644.
Horowitz, S.H. et al. (1991) "Computed tomographic-anglographic findings within the first 5 hours of cerebral infarction" *Stroke*, 22:1245-1253.
Hua, P. et al. (Jan. 1993) "Using Compound Electrodes in Electrical Impedance Tomography" *IEEE Transactions on Biomedical Engineering*, 40(1):29-34.
Jacquy, J. et al. (1974) "Cerebral Blood Flow and Quantitative Rheoencephalography" *Electroencephalography and Clinical Neurophysiology*, 37:507-511.
Jevning, R. et al. (Jan. 1989) "Evaluation of Consistency Among Different Electrical Impedance Indices of Relative Cerebral Blood Flow in Normal Resting Individuals" *J. Biomed. Eng.*, 11(1):53-56.
Johnston, I.H. and J.O. Rowan (1974) "Raised intracranial pressure and cerebral blood flow" *J. Neurol. Neurosurg. Psychiatry*, 37(4):392-402.
Johnston, S.C. et al. (2006) "National Stroke Association Guidelines for the Management of Transient Ischemic Attacks" *Ann. Neurol.*, 60:301-313.
Keren, H. et al. (Mar. 2007) "Evaluation of a Noninvasive Continuous Cardiac Output Monitoring System Based on Thoracic Bioreactance" *Am. J. Physiol. Heart Circ. Physiol.*, 293:H583-H589.
Linderholm, P. et al. (2003) "Microelectrical Impedance Tomography for Biophysical Characterization of Thin Film Biomaterials" *Transducers, Solid-State Sensors, Actuators and Microsystems, 12th International Conference.* Boston, Jun. 8-12, 2003; p. 284-287.
Lovett Doust, J.W. and J.N. Lovett Doust (Sep. 1975) "Aspects of the Cerebral Circulation During Non-REM Sleep in Healthy Controls and Psychiatric Patients, as Shown by Rheoencephalography" *Psychophysiology*, 12(5):493-498.
Martinez, F.S. (2007) "Electrical Bioimpedance Cerebral Monitoring: Fundamental Steps Toward Clinical Application" Thesis for the Degree of Doctor of Philosophy, Department of Signals and Systems, Division of Biomedical Engineering, Chalmers University of Technology, Goteborg, Sweden & School of Engineering, University College of Boras, Boras, Sweden. 153 pages.
Moskalenko, Y.E. et al. (2001) "Slow Rhythmic Oscillations within the Human Cranium: Phenomenology, Origin, and Informational Significance" *Human Physiology*, 27(2):171-178, Translated From *Fiziologiya Cheloveka*, 27(2):47-55 (2001).
Ragauskas, A. et al. (2003) "Implementation of Non-Invasive Brain Physiological Monitoring Concepts" *Medical Engineering & Physics*, 25:667-678.
Schaefer, P.W. et al. (Jan. 2006) "First-Pass Quantitative CT Perfusion Identifies Thresholds for Salvageable Penumbra in Acute Stroke Patients Treated with Intra-arterial Therapy" *Am. J. Neuroradiol.*, 27(1):20-25.
Scheinberg, P. and E.A. Stead (Sep. 1949) "The Ceberal Blood Flow in Male Subjects As Measured By the Nitrous Oxide Technique. Normal Values for Blood Flow, Oxygen Utilization, Glucose Utilization, and Peripheral Resistance, With Observations on the Effect of Tilting and Anxiety" *J. Clin. Invest.*, 28(5):1163-1171.
Seipel, J.H. et al. (1962) "Cranial Impedance Plethysmography—Rheoencephalography as a Method of Detection of Cerebrovascular Disease" in *Cerebral Ischemia*. E. Simonson and T.H. McGavack (eds.), Springfield, Illinois: Charles C. Thomas, p. 162-179.
Seipel, J.H. and J.E. Floam (1975) "Rheoencephalographic and Other Studies of Betahistine in Humans: I. The Cerebral and Peripheral Circulatory Effects of Single Doses in Normal Subjects" *J. Clin. Pharmacol.*, 15:144-154.
Shendar, B.S. (Sep. 1991) "Application of Rheoencephalography to Study Physiological Responses Under Acceleration Stress" Interim Report prepared for Office of Naval Technology, Washington, DC, US. Report No. NADC-91127-60, 87 pages.
Sobesky, J. et al. (Mar. 2005) "Does the Mismatch Match the Penumbra?: Magnetic Resonance Imaging and Positron Emission Tomography in Early Ischemic Stroke" *Stroke*, 36:980-985.
Steiner, L. et al. (Apr. 2002) "Continuous Monitoring of Cerebrovascular Pressure Reactivity Allows Determination of Optimal Cerebral Perfusion Pressure in Patients With Traumatic Brain Injury" *Critical Care Medicine*, 30(4):733-738. Abstract.

(56) References Cited

OTHER PUBLICATIONS

Steiner, L.A. ad P.J.D. Andrews (2006) "Monitoring the Injured Brain: ICP and CBF" *Br. J. Anaesth.*, 97(1):26-38.

Stiefel, M.F. et al. (2005) "Reduced Mortality Rate in Patients With Severe Traumatic Brain Injury Treated With Brain Tissue Oxygen Monitoring" *J. Neurosurg.*, 103(5):805-811.

Traczewski, W. et al. (2005) "The Role of Computerized Rheoencephalography in the Assessment of Normal Pressure Hydrocephalus" *Journal of Neurotrauma*, 22(7):836-843.

Webster J.G. (Ed.) "Measurement of Flow and Volume of Blood" in *Medical Instrumentation: Application and Design.* 1997; pp. 332-371.

Weindling, A.M. et al. (1983) "Cerebral Haemodynamics in Newborn Babies Studied by Electrical Impedance" *Acta Paediatr. Scand. Suppl.*, 311:14-19.

Weindling, A.M. et al. (Sep. 1982) "Effect of Electrode Size on the contributions of Intracranial and Extracranial Blood Flow to the Cerebral Electrical Impedance Plethysmogram" *Med. & Biol. Eng. & Comput.*, 20:545-549.

Wintermark, M. et al. (Aug. 2005) "Comparative Overview of Brain Perfusion Imaging Techniques" *Stroke*, 36:e83-e99.

International Patent Application No. PCT/IB2012/000846, filed Feb. 8, 2012, by Orsan Medical Technologies, Ltd: International Search Report and Written Opinion, mailed Sep. 18, 2012 (8 pages).

\* cited by examiner

DEVICES AND METHODS FOR MONITORING CEREBRAL HEMODYNAMIC CONDITIONS

RELATED APPLICATION

This application claims the benefit of priority under 35 U.S.C. §119(e) of U.S. Provisional Application No. 61/441,248, filed Feb. 9, 2011, and U.S. Provisional Application No. 61/474,739, filed Apr. 12, 2011, both of which are incorporated herein by reference in their entirety.

TECHNICAL FIELD

Aspects of the present disclosure relate to detection, monitoring and/or analysis of signals characterizing cranial bioimpedance measurements, and the prediction of physiological brain conditions based on such analysis.

BACKGROUND

A number of cerebro-hemodynamic characteristics may be clinically useful for diagnosing strokes, trauma, and other conditions that can affect the functioning of the cerebrovascular system. These characteristics may include cerebral blood volume, cerebral blood flow, cerebral perfusion pressure, mean transit time, time to peak, intracranial pressure, and others. Conventional methods for detecting or monitoring these parameters may include physically inserting a probe into the cerebrospinal fluid or into an artery, angiography, computed tomography angiography (CTA), perfusion computed tomography (PCT), transcranial doppler ultrasound (TCD), positron emission tomography (PET), and magnetic resonance imaging (MRI) and angiography (MRA).

Some non-invasive methods for detecting or monitoring cerebro-hemodynamic parameters may require, for example, machines for carrying out CT, PCT, PET, and/or MRI procedures. In some instances, the cost of these machines, their limited mobility, and/or their significant expense per use, may limit their usefulness in situations where either regular, continuous, or frequent monitoring of cerebro-hemodynamic characteristics may be desirable.

The foregoing description is merely exemplary for providing general background and is not restrictive of the various embodiments of systems, methods, devices, and features as described and claimed.

SUMMARY OF A FEW ASPECTS OF THE DISCLOSURE

In the presently disclosed embodiments, several exemplary methods and systems are described that may be used to detect and monitor cerebrovascular hemodynamic characteristics. In some embodiments, these methods and systems may be useful, for example, for continuous or frequent use and may involve, for example, a patient headset and cerebral perfusion monitor for synchronizing and monitoring signals indicative of cerebrovascular hemodynamic characteristics. The patient headset and cerebral perfusion monitor may provide information for diagnosing changes in arterial occlusion, such as occlusions brought on by ischemic stroke or head trauma.

One exemplary disclosed embodiment may include a cerebro-hemodynamic measurement apparatus. The apparatus may include at least one processor configured to receive at least one signal characterizing at least one cranial bioimpedance measurement. The at least one processor may be further configured to correlate the at least one signal with timing of a cardiac wave. The at least one processor may be further configured to analyze the at least one signal during a time period defined by the cardiac wave to ascertain an extent of at least one expected characteristic in the at least one signal during the time period, and output information for predicting a physiological brain condition based on the extent of the at least one expected characteristic in the at least one signal.

In another embodiment, the at least one signal may include at least two bioimpedance signals, each relating to differing hemispheres of a subject's brain, wherein the at least two bioimpedance signals are synchronized to each other.

In other embodiments, the at least one expected characteristic may relate to at least one of height, delay, width, and timing of a feature in a bioimpedance signal, or may relate to at least one of a first peak, a second peak, and a third peak in a bioimpedance signal. The at least one expected characteristic may include one or more of a peak location, a minima location, an anticipated peak location, and an anticipated minima location.

In still other embodiments, the at least one signal may include a first signal relating to a first hemisphere of a subject's brain and a second signal relating to a second hemisphere of the subject's brain, wherein the processor is configured to predict a physiological brain condition based at least in part on a comparison of portions of the first signal with portions of the second signal.

In still another embodiment, the processor may be further configured to analyze portions of at least one of the first signal and the second signal during predetermined time periods of interest defined by a cardiac wave.

In another embodiment, analyzing may include fitting the at least one signal to a prediction based on an extent of correlation between the at least one expected characteristic and the at least one signal.

In yet another embodiment, the processor may be further configured to calibrate features in the at least one signal with cerebral blood flow image information.

In a further embodiment, analyzing may include focusing on a time period around an expected characteristic based on an indicated physiological condition.

In additional embodiments, correlating may include synchronizing the at least one signal with timing of a simultaneous cardiac cycle. Correlating may also include detecting a coincidence in timing of the at least one signal with a cardiac cycle by comparing portions of the at least one signal with a known signal previously correlated to a cardiac cycle.

Cardiac waves used for correlation may include any repeating portion of an ECG. Cardiac waves used for correlation may also be an ECG R wave. The time period defined by the cardiac wave my included at least two repetitions of a cardiac cycle.

The foregoing summary and following description of drawings and following detailed description are exemplary of a just a few aspects of the disclosure, are explanatory only, and are not restrictive of the invention, as claimed.

BRIEF DESCRIPTION OF THE DRAWINGS

The accompanying drawings, which are incorporated in and constitute a part of this specification, together with the description, serve to explain the principles of the embodiments described herein.

DETAILED DESCRIPTION

Reference will now be made in detail to exemplary embodiments as with reference to the accompanying drawings. Wherever possible, the same reference numbers will be used throughout the drawings and the following description to refer to the same or like parts. These embodiments are described in sufficient detail to enable those skilled in the art to practice the invention and it is to be understood that other embodiments may be utilized and that changes may be made without departing from the scope of the present invention. The following detailed description, therefore, is not to be interpreted in a limiting sense.

Unless otherwise defined, all technical and/or scientific terms used herein have the same meaning as commonly understood by one of ordinary skill in the art to which the embodiments of the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Exemplary disclosed embodiments may include devices and methods for the detection and monitoring of signals characterizing bioimpedance measurements. More specifically, they may include apparatuses for receiving, correlating, and analyzing signals and outputting information for predicting a physiological brain condition.

Embodiments consistent with the present disclosure may include a cerebro-hemodynamic measurement apparatus. Such an apparatus may include elements and features suited to facilitate the measurement of cerebro-hemodynamic characteristics. A cerebro-hemodynamic measurement apparatus may include (but do not necessarily include), for example, support elements such as a headset, headband, or other framework elements to carry or house additional functional elements. Further structures that may be incorporated may include electrodes, circuitry, processors, sensors, wires, transmitters, receivers, and other devices suitable for obtaining, processing, transmitting, receiving, and analyzing electrical signals. A cerebro-hemodynamic measurement apparatus may additionally include fasteners, adhesives, and other elements to facilitate attachment to a subject's body. As used herein, a cerbro-hemodynamic measurement apparatus need not include all such features.

Figure 1:
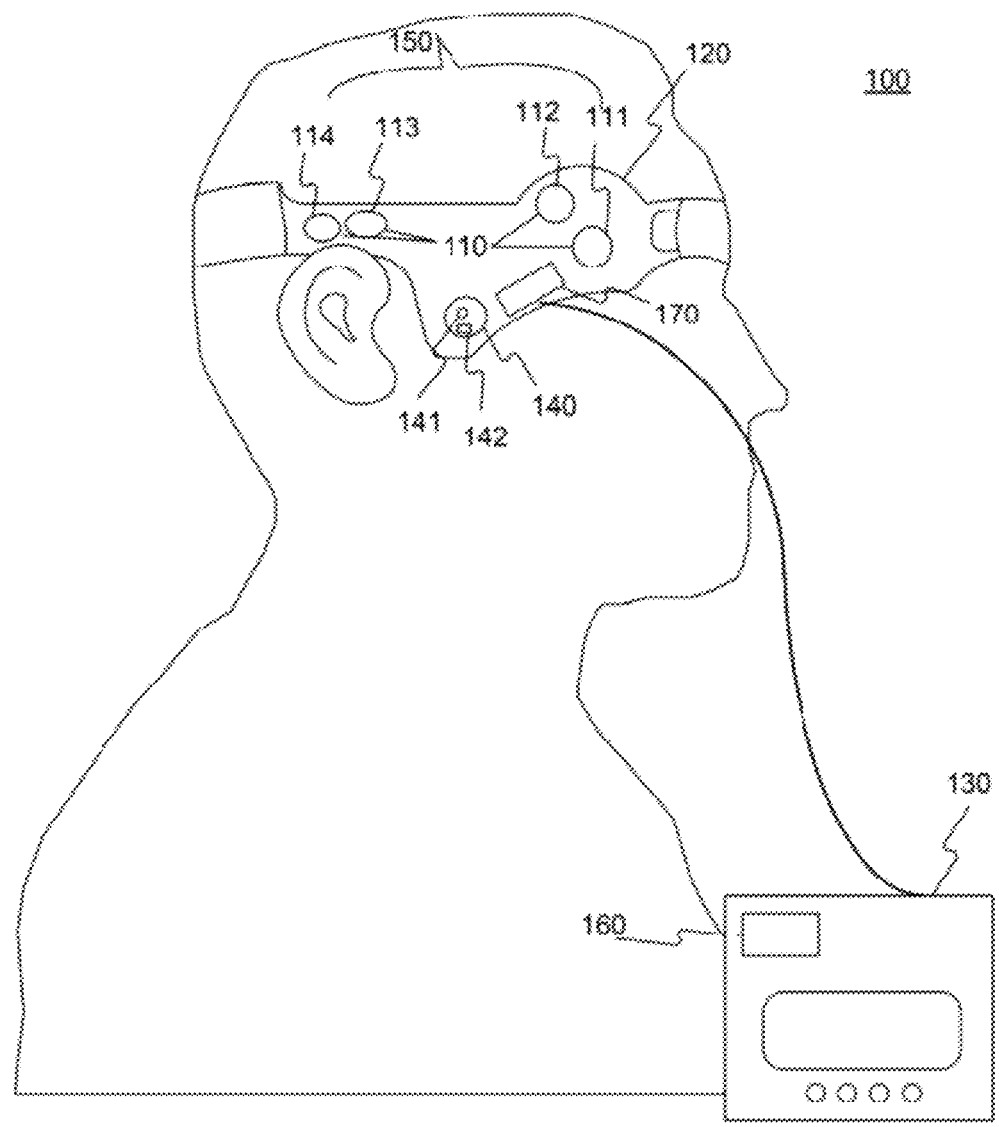
FIG. 1 provides a diagrammatic representation of an exemplary cerebro-hemodynamic measurement apparatus consistent with exemplary embodiments of the invention.

FIG. 1 provides a diagrammatic representation of an exemplary cerebro-hemodynamic measurement apparatus 100. This exemplary apparatus 100 may include electrodes 110 affixed to a subject's head via a headset 120. Electrodes 110 may be connected to cerebral perfusion monitor 130 via wires (or may alternatively include a wireless connection).

In some exemplary embodiments consistent with the disclosure, a cerebro-hemodynamic measurement apparatus may include at least one processor configured to perform an action. As used herein, the term "processor" may include an electric circuit that performs a logic operation on an input or inputs. For example, such a processor may include one or more integrated circuits, microchips, microcontrollers, microprocessors, all or part of a central processing unit (CPU), graphics processing unit (GPU), digital signal processors (DSP), field-programmable gate array (FPGA) or other circuit suitable for executing instructions or performing logic operations. The at least one processor may be configured to perform an action if it is provided with access to, is programmed with, includes, or is otherwise made capable carrying out instructions for performing the action. The at least one processor may be provided with such instructions either directly through information permanently or temporarily maintained in the processor, or through instructions accessed by or provided to the processor. Instructions provided to the processor may be provided in the form of a computer program comprising instructions tangibly embodied on an information carrier, e.g., in a machine-readable storage device, or any tangible computer-readable medium. A computer program may be written in any form of programming language, including compiled or interpreted languages, and it can be deployed in any form, including as a standalone program or as one or more modules, components, subroutines, or other unit suitable for use in a computing environment. The at least one processor may include specialized hardware, general hardware, or a combination of both to execute related instructions. The processor may also include an integrated communications interface, or a communications interface may be included separate and apart from the processor. The at least one processor may be configured to perform a specified function through a connection to a memory location or storage device in which instructions to perform that function are stored.

Consistent with some embodiments of the invention, the at least one processor may be configured to receive a signal. As used herein, a signal may be any time-varying or spatially-varying quantity. Receiving a signal may include obtaining a signal through conductive means, such as wires or circuitry; reception of a wirelessly transmitted signal; and/or reception of a signal previously recorded, such as a signal stored in memory. Receiving a signal may further encompass other methods known in the art for signal reception.

At least one processor 160, illustrated in FIG. 1, configured to receive, correlate, and analyze signals characterizing at least one cranial bioimpedance measurement may be included in Cerebral Perfusion Monitor 130, as part of exemplary cerebro-hemodynamic measurement apparatus 100. Processor 160 may be configured to perform all or some of the signal analysis methods described herein, or some of those functions might be performed by a separate processor. Processor 160 may also be configured to perform any common signal processing task known to those of skill in the art, such as filtering, noise-removal, etc. Processor 160 may further be configured to perform pre-processing tasks specific to the signal analysis techniques described herein. Such pre-processing tasks may include, but are not limited to, removal of signal artifacts, such as motion and respiratory artifacts.

A signal characterizing at least one bioimpedance measurement may include any type of signal containing information about the electrical impedance of a biological subject. Such a signal may contain information about the electrical impedance of the subject between any two portions of a subject's body. Information about the electrical impedance of the subject may include information about the resistive and/or reactive components of electrical impedance.

According to the present disclosure, in some exemplary embodiments a signal characterizing at least one cranial bioimpedance measurement may be a bioimpedance signal, such as an impedance plethysmography signal, or a photo-plethysmography signal. A bioimpedance signal may include at least one voltage signal, and/or at least one current signal. A bioimpedance signal may include two or more voltage and/or current signals, and may include a signal representative of a comparison between two or more voltage and/or current signals. A bioimpedance signal may be measured as a response to at least one measurement voltage signal, and/or at least one measurement current signal. In a bioimpedance signal, information about the electrical impedance of a subject's body may be contained in the amplitude, frequency, or phase angle of the signal. Information about the electrical impedance of a subject's body may also be contained in a comparison between the amplitudes, frequencies, or phase angles of multiple signals. Bioimpedance signals may be indicative, for example, of hemodynamic characteristics within a first and/or a second hemisphere of a subject's brain. Hemodynamic characteristics may include, for example, cerebral blood volume, cerebral blood flow, cerebral perfusion pressure, intracranial pressure, and any other parameter that might be at least partially reflective of cerebral conditions. First and second hemispheres may refer to right and left hemispheres of a subject's brain, in any order. A signal indicative of hemodynamic characteristics within a particular side of a subject's brain may be obtained from the same side of the subject's head, via electrodes or the like, or may be obtained from an opposite side of the subject's head. A signal indicative of hemodynamic characteristics within a particular side of a subject's brain may also be obtained from other locations, such as on the neck of a subject, where, for example, carotid arteries are located.

Processor 160 may be configured to receive a signal from one or more electrodes 110, included in exemplary headset 120 of FIG. 1. Electrodes 110, which may be arranged singly, in pairs, or in other appropriate groupings, depending on implementation. The electrodes on exemplary headset 120 may be arranged so as to obtain bioimpedance signal waveforms. Bioimpedance may be measured by two sensor sections 150, disposed on the right and left sides of the head to correspond with the right and left hemispheres of the brain, for example. While only one sensor section 150 is shown in FIG. 1, an opposite side of the subject's head might include a similar electrode arrangement. Each sensor section 150 may include one pair of front electrodes, front current electrode 111 and front voltage electrode 112, and one pair of rear electrodes, rear current electrode 114, and rear voltage electrode 113. The distance between the pairs may be adjusted such that a particular aspect of a cerebro-hemodynamic condition is measured, as will be discussed later in greater detail. The electrode configuration depicted in FIG. 1 is only one example of a suitable electrode configuration. Additional embodiments may include more or few electrodes 110, additionally or alternatively arranged in different areas of exemplary headset 120. Other embodiments may include electrodes 110 configured on an alternatively shaped headset to reach different areas of the subject's head then the exemplary headset 120.

Pairs of electrodes 110 may include a current output electrode and a voltage input electrode. For instance, front current electrode 111 and front voltage electrode 112 may form an electrode pair. In one embodiment, an output current may be generated by cerebral perfusion monitor 130 and passed between front current electrode 111 and rear current electrode 114. The output current may include an alternating current (AC) signal of constant amplitude and stable frequency. An input voltage induced on the head due to the output current may be measured between front voltage electrode 112 and rear voltage electrode 113. An input voltage may be measured at the same frequency as the output current. A comparison between the output current signal and the input voltage signal may yield information related to the bioimpedance of the subject. More specifically, an amplitude of the bioimpedance may be computed as a ratio of the input voltage signal amplitude to the output current amplitude signal, and a phase of the bioimpedance may be computed as the phase difference by which the output current signal leads the input voltage signal.

A bioimpedance signal may also include output current at more than a single AC frequency. The output current may include a set of predefined frequencies and amplitudes, with detection of the measured voltage at all the frequencies or a part of the frequency range.

In another embodiment, a first bioimpedance signal and a second bioimpedance signal may include output AC currents at different frequencies. For example, the current outputted by electrodes located on one side of the head may be at one frequency and the current outputted by the electrodes located on the other side of the head may be at a different frequency. Detection of the voltage may be at one frequency, the other frequency, or both frequencies by proper filtering and analysis.

Blood flow into and out of the head, and more specifically, the brain, during a cardiac cycle may result in a cyclic change of the bioimpedance measured by electrodes 110. Bioimpedance changes may correlate with blood content in the head and brain. In general, because blood has a relatively low impedance when compared with tissue found in the head, higher blood content results in lower impedance. Blood flow into brain tissue may also vary the frequency response of the brain impedance. Comparing bioimpedance measurements at different frequencies may provide additional information indicative of hemodynamic characteristics.

The exemplary headset 120 may include further devices or elements for augmenting bioimpedance measurements or for performing measurements in addition to bioimpedance measurements, such as an additional sensor or sensors 140. In one embodiment, additional sensor 140 may include, for example, a light emitting diode 141 and a photo detector 142 for performing Photo Plethysmography (PPG) measurements either in conjunction with or in alternative to bioimpedance signal measurements. The exemplary headset 120 may further include various circuitry 170 for signal processing or other applications and may include the capability to transmit data wirelessly to cerebral perfusion monitor 130 or to other locations. In an additional embodiment, cerebral perfusion monitor 130 may be integrated with headset 120. Although illustrated in the example of FIG. 1, additional sensor 140 and circuitry 170 may be omitted.

Exemplary headset 120 may include various means for connecting, encompassing, and affixing electrodes 110 to a patient's head. For example, headset 120 may include two or more separate sections that are connected to form a loop or a band that circumscribes the patient's head. Any of these aspects, including bands, fasteners, electrode holders, wiring, hook-and-loop connector strips, buckles, buttons, clasps, etc. may be adjustable in order to fit a patient's head. Portions of exemplary headset 120 may be substantially flexible and portions of the exemplary headset 120 may be substantially inflexible. For example, electrode-including portions of exemplary apparatus 120 may be substantially inflexible in order to, among other things, substantially fix electrodes 110 in specific anatomical positions on the patient's head. In addition to or in the alternative, other portions, such as bands or connectors holding the exemplary headset 120 to a patient's head, may be substantially flexible, elastic and/or form fitting.

Any portion of exemplary headset 120 may be specifically designed, shaped or crafted to fit a specific or particular portion of the patient's anatomy. For example, portions of exemplary headset 120 may be crafted to fit near, around or adjacent to the patient's ear. Portions of exemplary headset 120 may be specifically designed, shaped or crafted to fit the temples, forehead and/or to position electrodes 110 in specific anatomical or other positions. Portions of the exemplary headset 120 may be shaped such that electrodes 110 (or other included measurement devices) occur in specific positions for detecting characteristics of blood flow in the head or brain of the patient. Examples of such blood flow may occur in any of the blood vessels discussed herein, especially the arteries and vasculature providing blood to the head and/or brain, regardless of whether the vessels are in the brain or feed the brain.

Exemplary headset 120 may include features suitable for improving comfort of the patient and/or adherence to the patient. For example exemplary headset 120 may include holes in the device that allow ventilation for the patient's skin. Exemplary headset 120 may further include padding, cushions, stabilizers, fur, foam felt, or any other material for increasing patient comfort.

As mentioned previously, exemplary headset 120 may include one or more additional sensors 140 in addition to or as an alternative to electrical or electrode including devices for measuring bioimpedance. For example, additional sensor 140 may include one or more components configured to obtain PPG data from an area of the patient. Additional sensors 140 may comprise any other suitable devices, and are not limited to the single sensor illustrated in FIG. 1. Other examples of additional sensor 140 include devices for measuring local temperature (e.g., thermocouples, thermometers, etc.) and/or devices for performing other biomeasurements.

Exemplary headset 120 may include any suitable form of communicative mechanism or apparatus. For example, headset 120 may be configured to communicate or receive data, instructions, signals or other information wirelessly to another device, analytical apparatus and/or computer. Suitable wireless communication methods may include radiofrequency, microwave, and optical communication, and may include standard protocols such as Bluetooth, WiFi, etc. In addition to, or in alternative to these configurations, exemplary headset 120 may further include wires, connectors or other conduits configured to communicate or receive data, instructions, signals or other information to another device, analytical apparatus and/or computer. Exemplary headset 120 may further include any suitable type of connector or connective capability. Such suitable types of connectors or connective capabilities may include any standard computer connection (e.g., universal serial bus connection, firewire connection, Ethernet or any other connection that permits data transmission). Such suitable types of connectors or connective capabilities may further or alternatively include specialized ports or connectors configured for the exemplary apparatus 100 or configured for other devices and applications.

Figure 2:
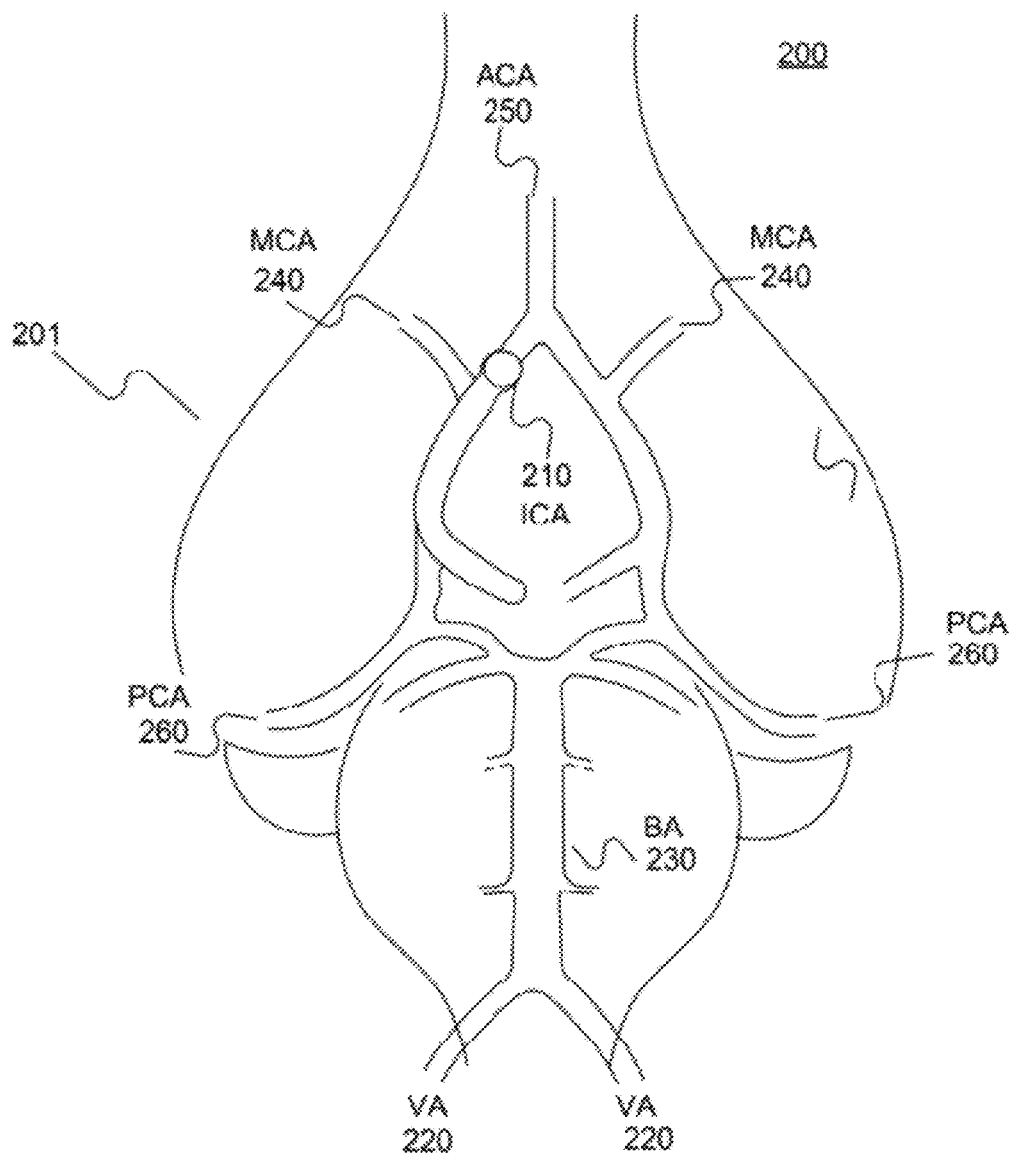
FIG. 2 provides a diagrammatic representation of major cerebral arteries.

FIG. 2 provides a diagrammatic representation of major features of the cerebral vasculature 200. The cerebral vasculature in FIG. 2 is viewed from below the brain, with the top of the page representing the front of a subject. The blood supply to the brain 201 comes from four main arteries traversing the neck. The larger two are the right and left internal carotid arteries (ICA) 210, in the front part of the neck. The vertebral arteries (VA) 220 are located in the back of the neck and join to form the basilar artery (BA) 230. The internal carotid arteries and the basilar arteries are connected by Posterior Communicating Artery (not shown) and Anterior Communicating Artery (not shown) to form the Circle of Willis (COW). In an ideal patient, the COW is a network of connected arteries that allows blood supply to the brain 201 even when one or more of the feeding arteries is blocked.

The main arteries that supply blood to the brain 201 are the Middle Cerebral Arteries (MCAs) 240, Anterior Cerebral Arteries (ACAs) 250, and Posterior Cerebral Arteries (PCAs) 260. The MCAs 240 may be one area of interest when diagnosing decreased blood flow to portions of the brain 201. The MCAs 240 are the sole blood supply to the largest brain region—about two thirds of each brain hemisphere.

The electrodes of exemplary headset 120 may be placed such that signal pathways coincide, cross, or interact to some extent with the MCAs 240 or other arteries. For example, electrodes 110 may be positioned to straddle the MCA 240, such that the MCA 240 runs between a pair of planes dissecting the head and extending through each electrode. Thus, measures of signal properties such as impedance may be indicative of and/or related to blood flow in an MCA 240 or other arteries. Specific electrode 110 placement in and around the patient's temples, facilitated by specific configurations of headset 120, for example, may enable generation of signals including information relating to blood flow in the MCA 240, in particular. The electrodes may, for instance, be 70 mm to 90 mm apart. The electrodes may also be located at specific locations on the head. For example, a first pair 111 and 112 of electrodes may be arranged on the forehead below the hair line and a second pair 113 and 114 above the ear under the upper part of the ear lobe. In these locations, the electrodes may be placed directly on bare skin and not on hair, and may achieve better electrical contact and better adhesion, than on hairy areas of the scalp, although the invention may be used in connection with electrode placement in other locations, including the scalp. The electrodes may also be placed away from external facial arteries and away from extensive muscle groups like the eye muscles.

Figure 3:
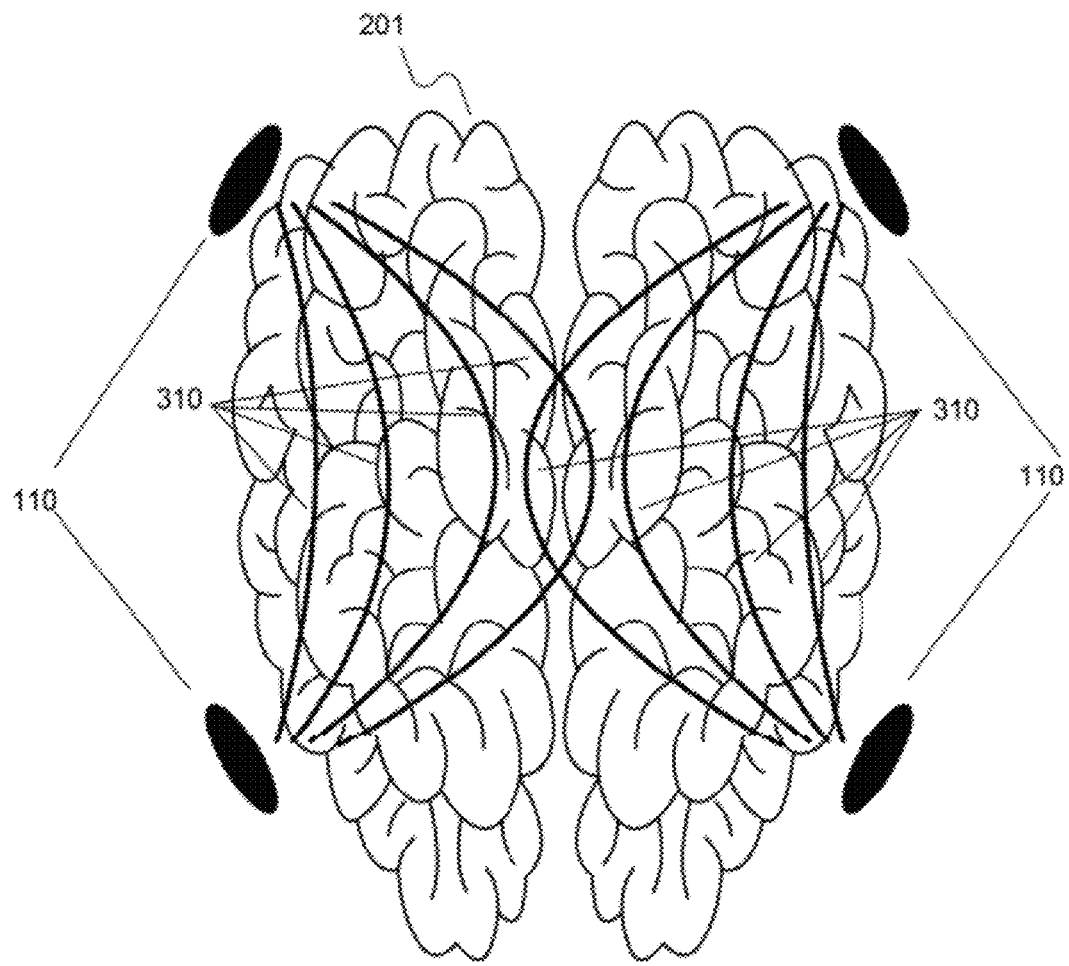
FIG. 3 provides a diagrammatic representation of exemplary bioimpedance signal pathways in the brain of a subject consistent with exemplary embodiments of the invention.

FIG. 3 provides a diagrammatic representation of exemplary bioimpedance signal pathways 310 in the brain 201 of a subject. The exemplary configuration illustrates multiple signal pathways 310 through each of the right and left brain hemispheres. The multiple signal pathways extend between electrodes 110 affixed to the head of a subject via headset 120. The impedance of the signal pathways 310 may be influenced by the presence or absence of blood along the pathway, because blood has a relatively low impedance. At least some of the signal pathways 310 may be coincident with brain vasculature. Signal properties may thus be measured that are indicative of hemodynamic characteristics, such as blood volume, in the blood vessels of the brain 201. Changes in bioimpedance may thus be indicative of changes in blood flow in the brain 201. Signal pathways 310 depicted in FIG. 3 are representative of only a small number of an infinite number of pathways which may exist in the general area of signal pathways 310.

In some embodiments consistent with the present disclosure, the at least one signal characterizing at least one cranial bioimpedance measurement may include at least two bioimpedance signals, each relating to differing hemisphere's of a subject's brain. A bioimpedance signal relating to a particular hemisphere of a subject's brain, as used herein, may include a bioimpedance signal reflective of impedance characteristics of the side of the brain to which it relates. A bioimpedance signal relating to a particular side of a subject's brain may be obtained from the same side of the subject's head, via electrodes or the like, or may be obtained from an opposite side of the subject's head. A bioimpedance signal relating to a particular side of a subject's brain may also be obtained from other locations, such as on the neck of subject, where, for example, carotid arteries are located.

According to embodiments consistent with the present disclosure, the at least one signal characterizing at least one cranial bioimpedance measurement may include a first signal relating to a first hemisphere of a subject's brain and a second signal relating to a second hemisphere of a subject's brain. An exemplary representation of first and second bioimpedance signals relating to first and second hemispheres of subject's brain may be explained with reference to FIG. 4.

Figure 4:
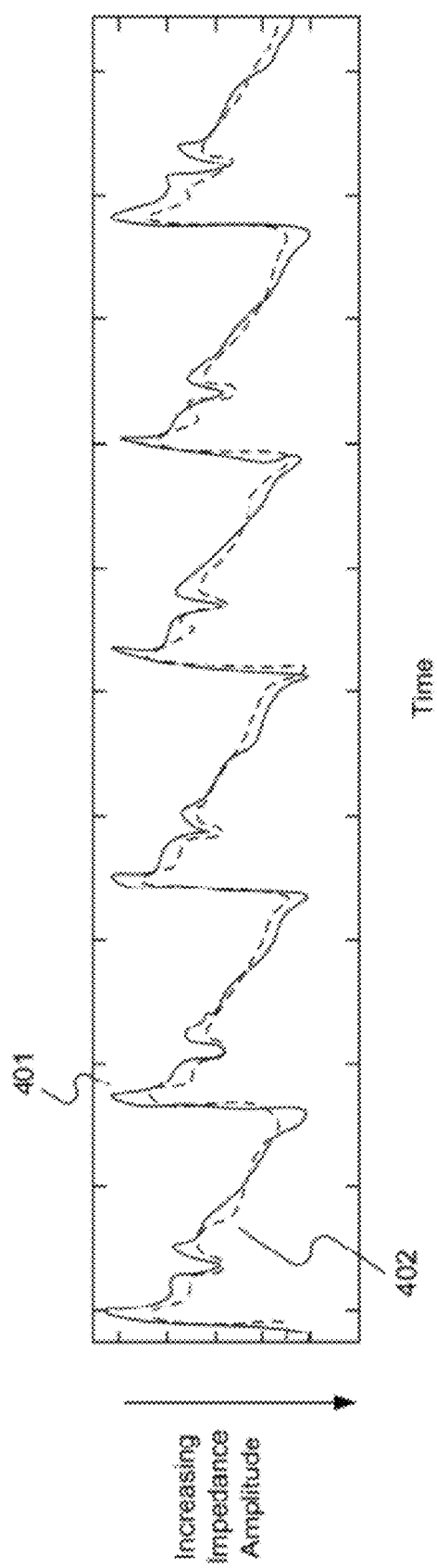
FIG. 4 provides a diagrammatic representation of an exemplary bioimpedance signal obtained from a cerebro-hemodynamic measurement apparatus consistent with exemplary embodiments of the invention.

FIG. 4 provides a diagrammatic representation of exemplary bioimpedance signals 401, 402 obtained from a cerebro-hemodynamic measurement apparatus, such as apparatus 100. The illustrated bioimpedance signals 401, 402 show a periodic change of impedance amplitude for right and left brain hemispheres, respectively, of a relatively healthy patient, as measured using an exemplary apparatus 100. Thus, signals 401 and 402 are examples of first and second bioimpedance signals relating to first and second hemispheres of subject's brain.

Consistent with embodiments of the present disclosure, two bioimpedance signals may be synchronized to each other. As used herein, synchronization may be performed, for example, with respect to a common reference timeframe, wherein the signals in the reference timeframe do not differ by more than a specified amount of time from each other as compared to their actual occurrence. For example, two signals obtained from different sources may simultaneously reflect an identical event. However, due to equipment, signal processing, or other limitations, the timeframes within which these signals are recorded may differ. Thus, the event may appear to have occurred at one time in a first signal and a different time in a second signal. By synchronizing the signals to within a specified amount of time from of each other, the signals may then be viewed in a common reference timeframe. In the common reference timeframe, the occurrence of the event, simultaneously recorded by both signals, may not differ by more than a specified amount of time between the first signal and the second signal.

Synchronization may occur, for example, on an independent scale, or may occur with reference to a biologic scale. One example of a biologic scale may be defined by ECG. Specifically, timing of the bioimpedance waveform signals (or portions thereof) from opposite brain hemispheres may be synchronized to a scale defined by ECG. In one embodiment, this synchronization may occur to within 40 ms. Longer synchronization schemes may be used consistent with the invention as can shorter schemes. For example, synchronization of signals may be performed to within milliseconds of each other. Non-limiting examples of timing synchronization may include synchronization to within about 40 ms, about 30 ms, about 20 ms, about 10 ms and about 5 ms. In other embodiments, the waveforms may be synchronized to within 5 ms of one another or to within fractions of a millisecond, such as, for example, to within 0.1 ms or less. Such a synchronization analysis may be performed while bioimpedance signal waveforms are being collected and may be performed on recorded bioimpedance signal waveforms stored in a memory (e.g., external or computer memory). Signals may be synchronized to each other through various means, including the use of timing equipment and reference features within the signals.

In another embodiment, two signals may be synchronized on an independent time scale, without the use of an ECG signal. Waveforms for right and left brain hemispheres, for example, may be synchronized using at least one processor included within precision timing equipment such that data is extracted from both hemispheres simultaneously or with a known temporal relationship. For example, waveforms may be synchronized to within several milliseconds such that features such as peak onset, for example, can be related. Alternatively, or in addition to equipment-based synchronization, signals may be synchronized based on features in the waveform. Features of a cardiac electric signal may be commonly detected in the waveforms extracted from each brain hemisphere. For example, a cardiac R wave, the electrical signal preceding a heartbeat, may be detected from a ECG signal measured in parallel to the bioimpedance signal waveform from each hemisphere. Therefore, the waveforms from different hemispheres, for example, may be synchronized using the detection or identification of R wave onset in the ECG waveform. The waveforms from different hemispheres, for example, may also be synchronized using the detection or identification of any other portion of a cardiac cycle. Such a synchronization analysis may be performed while bioimpedance signal waveforms are being collected (e.g., in real time) or performed on recorded bioimpedance signal waveforms stored in memory (e.g., non-real time).

By determining timing delays between features of signals received from the right and left hemispheres, different information about cerebral hemodynamic characteristics may be provided. Such timing delays may be between entire bioimpedance waveforms, or only portions of waveforms. For example, delays may be examined for a particular features of a waveform, or for various combinations thereof. In some embodiments, delays may only be considered significant if they pass a particular threshold. Under some conditions, greater delays may indicate an exacerbated condition as compared to shorter delays. Furthermore, changes over time in the duration of delay may indicate either an improving or deteriorating condition. In some embodiments, changes in timing delays over time may be monitored. A decrease in delay over a treatment period may indicate that the patient's cerebrovascular condition is improving, while an increase in delay may indicate that a patient's condition is worsening.

Synchronizing signals may also permit a reduction in effects caused by heart rate variance when comparing signals. Variation in heart rate results in changes in the length of cardiac cycles. As a result, timing of corresponding features in a signal may vary due heart rate variance. Thus, analyzing the timing of features within unsynchronized waveforms may be affected by variations in heart rate. Determining differences between two synchronized signals may thus reduce the effects of heart rate variation.

In accordance with some embodiments of the present disclosure, the at least one processor may be configured to correlate the at least one signal with timing of a cardiac wave. The at least one signal may be correlated with the timing of a cardiac wave based on any features within either the signal waveform or the cardiac waveform. Correlating a signal with the timing of a cardiac wave may involve relating features of the signal to features of the cardiac wave.

Exemplary methods for correlating a signal with the timing of a cardiac wave may be described with reference to FIG. 4. As shown in FIG. 4, bioimpedance amplitude may exhibit a periodic cycle for both left and right brain hemispheres. The period of this change in amplitude is approximately the period of a cardiac cycle. In FIG. 4, the y-scale is inversely correlated with impedance amplitude. That is, high values of impedance amplitude are reflected by low values in the signal as illustrated in FIG. 4. More specifically, each cardiac cycle begins with a decrease in impedance that corresponds to a rapid increase in blood flow, reflected in the signal peaks illustrated in FIG. 4. The maxima shown (i.e., the signal peaks) in each periodic cycle in FIG. 4 are indicative of impedance minima that correspond to a maximal blood flow. This maximal blood flow may closely follow ventricular systole, i.e. the heart contraction which forces blood through the vascular system. In turn, ventricular systole may be reflected in the R wave of a cardiac ECG. The cardiac R wave and a bioimpedance signal waveform maximum may therefore be related events. A processor may thus be configured to recognize this relationship and correlate a signal with the timing of a cardiac wave. Any portions of either a signal or a cardiac wave may be used for correlation.

While FIG. 4 illustrates variations in the amplitude of a bioimpedance signal waveform, information may also be obtained from the phase angle of a bioimpedance signal waveform. The amplitude and phase of a bioimpedance signal waveform may be influenced by both resistive and reactive components of the electrical impedance of a subject. Typically, reactive components of the electrical impedance of a subject may generate a phase difference in the measured bioimpedance signal. Both the amplitude and phase of a bioimpedance signal, therefore, analyzed separately or in combination, may be indicative of cerebro-hemodynamic characteristics.

Correlating a signal with the timing of a cardiac wave may also (or alternatively) include detecting a coincidence in timing of the at least one signal with a cardiac cycle by comparing portions of the at least one signal with a known signal previously correlated to a cardiac cycle. In this embodiment, a known signal, previously correlated to a cardiac cycle may provide information about the relationship of various features within a cardiac cycle and within a signal. For example, a previous correlation may provide information about a timing delay between a cardiac R-wave, representing ventricular systole, and a bioimpedance amplitude minimum, representing maximal blood flow. A portion of a new bioimpedance signal may be compared with a corresponding portion of the known, previously correlated bioimpedance signal in order to detect corresponding timing delays between the new bioimpedance signal and a new cardiac cycle.

Correlating at least one signal with the timing of a cardiac wave may further (or alternatively) include synchronizing the at least one signal with timing of a simultaneous cardiac cycle. Such synchronization may be performed, for instance, with measuring equipment, ensuring that the at least one signal is obtained with a common reference timeframe to another signal representing the cardiac cycle—an ECG signal for instance. Such synchronization may also be performed by analyzing the at least one signal and another signal representing the cycle. The signals may be synchronized by using any portion of a cardiac cycle as a common event. In this example, a portion of a cardiac cycle may be simultaneously detected in the signal. The signal may then be synchronized with reference to that portion of the cardiac cycle. Non-limiting examples of timing synchronization between a signal characterizing a bioimpedance measurement and a cardiac cycle may include synchronization to within about 40 ms, about 30 ms, about 20 ms, about 10 ms and about 5 ms. In other embodiments, the waveforms may be synchronized to within 5 ms of one another or to within fractions of a millisecond, such as, for example, to within 0.1 ms or less. In some embodiments consistent with the present disclosure, a signal may be synchronized with reference to a cardiac R wave.

In accordance with some embodiments, at least one processor may be configured to analyze the at least one signal during a time period defined by the cardiac wave to ascertain an extent of at least one expected characteristic in the at least one signal during the time period.

Figure 5:
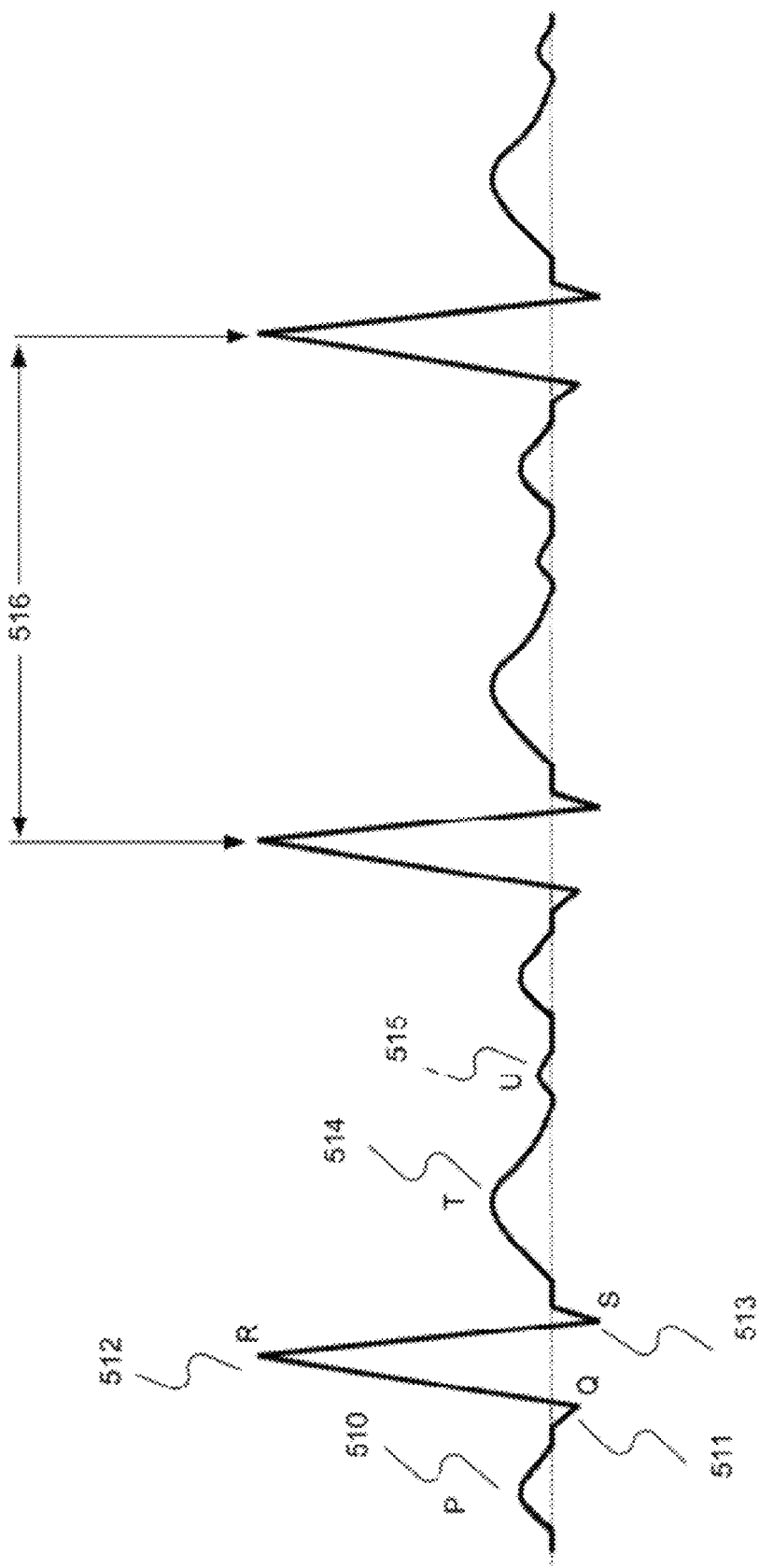
FIG. 5 provides a diagrammatic representation of an exemplary ECG signal, representative of a cardiac wave.

A cardiac wave may define a time period during which to analyze the at least one signal. FIG. 5 provides a diagrammatic representation of an exemplary ECG signal, representative of a cardiac wave. Illustrated in FIG. 5 are a P wave 510, Q wave 511, R wave 512, S wave 513, T wave 514, and U wave 515. As previously described, a cycle of a signal waveform, such as a bioimpedance signal waveform, may approximately correspond to a cardiac cycle. The signal may therefore be correlated to the timing of the cardiac cycle. Any features of a cardiac wave, including any of the P 510, Q 511, R 512, S 513, T 514, and U 515 waves, may be used to as a reference point to define the time period. For instance, a time period may be defined by the R wave 512 peak of a first cardiac cycle and the R wave 512 peak of a second cardiac cycle. The second cardiac cycle may be consecutive to the first cardiac cycle, making the time period the length of one cardiac cycle, as in the illustrated exemplary time period 516. The second cardiac cycle may also be non-consecutive with the first cardiac cycle, making the time period the length of two or more cardiac cycles. The time period may also be defined by different waves in the first and second cardiac cycles, for instance, by a P wave in a first cardiac cycle and an R wave in a second cardiac cycle. The time period may also be shorter than the length of a single cardiac cycle, defined, for instance, by a Q wave 511 and an S wave 513 as reference points within a single cardiac cycle. The time period for analysis may be predetermined or dynamically determined based on physiological conditions. In some embodiments, two or more time periods may be used for analysis. And in some embodiments, portions of two or more signals may be analyzed during the time period or time periods.

Expected characteristics of a bioimpedance signal may include any detectable features within the waveform that may be detected and analyzed. Expected characteristics may also include anticipated waveform features for which a processor is configured to look. Expected characteristics may be detectable through visual observation of a waveform, or may be detectable only through mathematical analysis of a waveform. An expected characteristic may be defined by a single aspect of a waveform, such as maximum amplitude, or may be defined by a relationship between multiple aspects of a waveform, such as relative peak height. A bioimpedance signal waveform may be wholly or partially characterized by expected characteristics.

Examples of expected characteristics may include local or global maxima and minima, i.e., peaks and valleys, inflection points, relative maxima height, relative minima depth, width of features, timing of features, delay of features, height and width ratios of maxima, depth and width ratios of minima, curvature at maxima nad minina, and ratios of any other aspects of maxima and minima. Expected characteristics may further include frequency spectrum aspects of a waveform, including power spectrum and phase angle. Other expected characteristics may include average waveform amplitudes over windows or ranges, or waveform slopes. Furthermore, multi-variate analysis may be used to define expected characteristics that include aspects of several maxima, minima, and/or any other aspects of the waveforms (e.g., background amplitude, noise, amplitude over certain intervals, etc.) Expected characteristics described herein are for exemplary purposes only, and are not intended to limit any embodiments of the disclosed methods and systems.

In some embodiments consistent with the present disclosure, expected characteristics of a bioimpedance waveform may include any of a first peak, a second peak, a third peak, a first minimum, a second minimum, and a third minimum. As used herein, the first, second, and third peaks may include local maxima within a signal waveform, and the first, second, and third minimum may include local minima within a signal waveform. These peaks and minima may be, for example, local maxima and minima within a single period of a cyclically repeating waveform. The peaks and minima may also include, for example, local maxima and minima within a waveform averaged over two or more signal cycles. Peaks and minima may also include, for example, local maxima and minima within a waveform determined for a specific heart rate, such as the most common heart rate in a time interval. As used herein, peaks and minima may correspond to absolute highs and lows, or may be indicative of a region where a high or low occurred. Exemplary expected characteristics may be further described with reference to FIG. 6.

Figure 6:
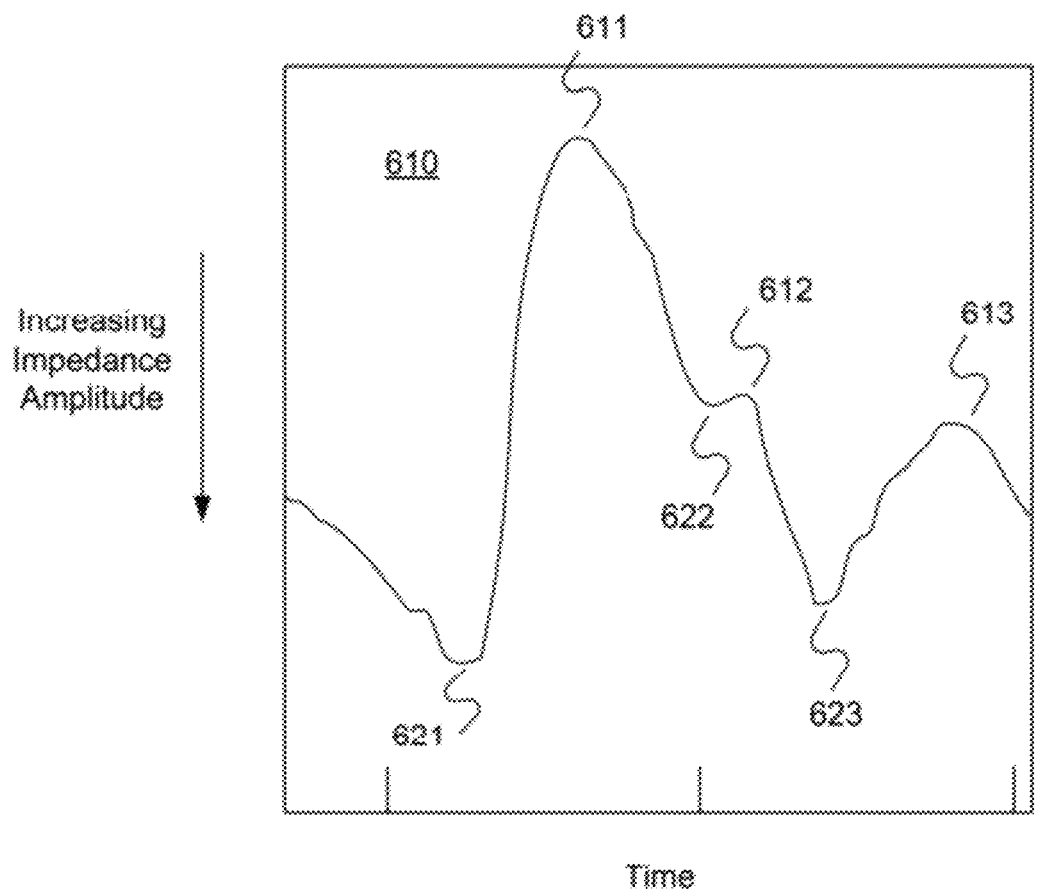
FIG. 6 provides a diagrammatic representation of some exemplary expected characteristics of a bioimpedance signal waveform time period, as defined by a single cardiac cycle.

FIG. 6 provides a diagrammatic representation of some exemplary expected characteristics of a bioimpedance signal waveform time period 610 defined by a single cardiac cycle. The waveform time period 610 corresponds to a cardiac cycle, and expected characteristics in the waveform may correspond to individual events in a cardiac cycle. For instance, a first peak P1, 611 may correspond to an initial rise in blood flow following aortic valve opening, which may correspond to minimum M0, 621. A second peak P2, 612 may correspond to a secondary rise in blood flow during the end of a systolic phase of the cardiac cycle, which may correspond to minimum M1, 622. A minimum M2, 623 may correspond to a decrease in blood flow as the aortic valve closes. A final peak P3, 613 may correspond to a final increase in blood flow before a continuous decline during a diastolic phase at the end of a cardiac cycle. For discussion purposes only, the expected characteristics illustrated in FIG. 6 are only some examples of expected characteristics that may be detected in a bioimpedance waveform. Furthermore, expected characteristics need not be confined to a single waveform period. An expected characteristic of a bioimpedance signal may, for example, be determined by analyzing the average amplitude of multiple corresponding maxima from different periods.

Furthermore, although FIG. 6 illustrates a biompedance signal waveform characterized by amplitude, methods and structures described herein may be used for the determination of signature features in other aspects of a bioimpedance signal waveform, for example, those characterized by a phase angle waveform. Phase angle aspects of a bioimpedance signal may respond differently than amplitude aspects of a bioimpedance signal, since phase angle changes correspond to changes in the reactive component of a bioimpedance signal. Analysis of phase angle aspects of bioimpedance signal waveforms may provide additional or different information about hemodynamic characteristics. Phase angle waveforms may be analyzed using any methods described herein with respect to amplitude waveforms, and by any additional methods known in the art. Phase angle waveforms of bioimpedance signals may be analyzed by themselves, and/or may be analyzed in comparison to or in conjunction with other bioimpedance signal aspects.

Figure 7A:
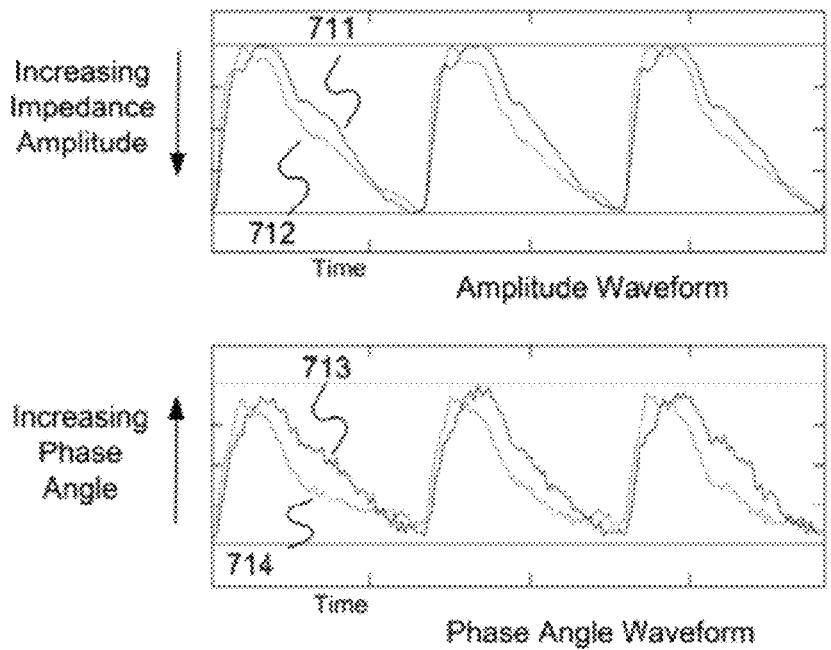
FIGS. 7a and 7b provide a diagrammatic representation of a comparison between amplitude and phase angle aspects of an exemplary bioimpedance signal waveform over multiple cardiac cycles, consistent with embodiments of the present invention.
Figure 7B:
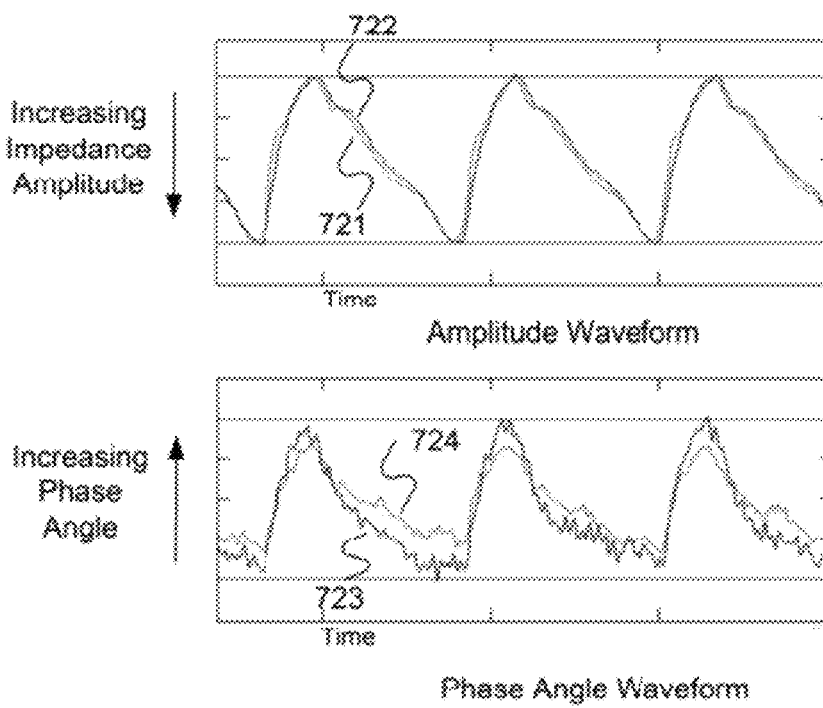

FIGS. 7a and 7b provide a diagrammatic representation of a comparison between exemplary amplitude and phase angle aspects of a bioimpedance signal waveform over multiple cardiac cycles. Under some conditions, as illustrated in FIG. 7a, phase angle waveforms may demonstrate similar characteristics as concurrently obtained amplitude waveforms. For example, in FIG. 7a, the delay between phase angle waveforms 713, 714 obtained from left (shown in black) and right (shown in gray) sides of the head, respectively, is similar to the delay in amplitude waveforms 711, 712 obtained from left (shown in black) and right (shown in gray) sides of the head, respectively. Such similarities in signature features between phase angle and amplitude aspects of a bioimpedance signal waveform may provide additional information for diagnosing a change in artery occlusion.

Phase angle waveforms may also demonstrate different characteristics than concurrently obtained amplitude waveforms, as illustrated in FIG. 7b for example. In FIG. 7b, the phase angle waveforms 723, 724 obtained from left (shown in black) and right (shown in gray) sides of the head, respectively, show a much larger asymmetry between left and right sides of the head than do the amplitude waveforms 721, 722 obtained from left (shown in black) and right (shown in gray) sides of the head, respectively. The peak of phase angle waveform 724, associated with a right side of the head is reduced compared to the peak of phase angle waveform 723, associated with the right side of the head. Furthermore, phase angle waveform 723 demonstrates a steeper decay from its peak. These differences do not appear in amplitude waveforms 721 and 722. Thus, differences in signature features of phase angle and amplitude waveforms of a bioimpedance signal may provide additional information for diagnosing a change in arterial occlusion.

Expected characteristics as illustrated in FIG. 6 may be detected through any type of analysis. In one embodiment, expected characteristics may be detected by finding inflection points in a measured waveform. In another embodiment, illustrated in FIG. 8, a pulse decomposition analysis may be conducted. Such detection analyses may be performed using at least one processor, such as at least one processor 160, described in connection with FIG. 1.

Figure 8:
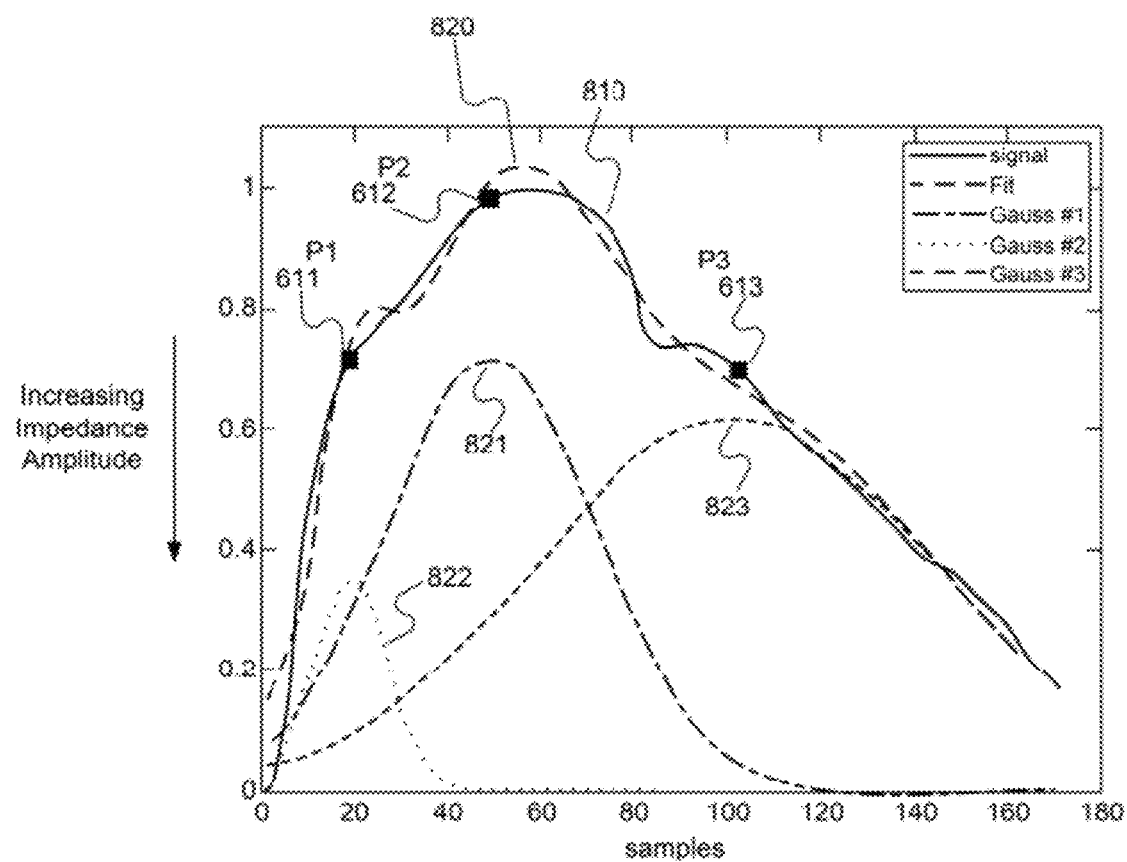
FIG. 8 provides a diagrammatic representation of a single bioimpedance signal waveform period as decomposed by a pulse decomposition algorithm for detecting expected characteristics in a bioimpedance signal, consistent with exemplary embodiments of the invention.

FIG. 8 provides a diagrammatic representation of a bioimpedance signal waveform period 810 as decomposed by a pulse decomposition algorithm for detecting expected characteristics in a bioimpedance signal. As discussed with respect to FIG. 6, a set of expected characteristics may comprise first, second and third peaks P1 611, P2 612, and P3 613, and minimums M0 621, M1 622 and M2 623, which may be computed, as shown in FIG. 6, based on inflection points in the bioimpedance signal waveform 611. A pulse decomposition algorithm represents one alternative method of computing expected characteristics. A pulse decomposition algorithm may parameterize a bioimpedance signal by using a combination of basic functions to approximate the bioimpedance signal.

A base function used for a best fit may be related to physiological pulse waveform functions or may have a general shape that resembles a physiological pulse and provides stable fit parameters. One example of a suitable base function is a Gaussian function. A Gaussian base function may provide a clear definition of pulse width and curvature, a stable fit algorithm, and full determination of higher derivatives. A pulse decomposition algorithm utilizing Gaussian base functions may be performed as described below, with reference to FIG. 8.

FIG. 8 provides a diagrammatic representation of three Gaussian base functions, first Gaussian 821, second Gaussian 822, and third Gaussian 823 computed as best fits to the second, first and third peak, P2 612, P1 611, and P3 613, respectively. Using ECG signals, a bioimpedance signal may be divided into individual waveforms 810, each corresponding to a cardiac cycle. A waveform minimum following the ECG R wave pulse may then be determined. Next, a waveform global maximum point following the minimum may be determined. It may then be determined whether the waveform global maximum point represents a first, second or third peak, P1 611, P2 612, or P3 613, based on a correspondence between the timing of the global maximum and previously obtained statistics. Next, a standard base function, such as a Gaussian, may be used to provide a best fit to the individual waveform near the determined global maximum, using timing and width limitations from previously obtained statistics. In FIG. 8, first Gaussian 821 is fitted to the highest peak P2 612. A best fit of the remaining two peaks, using second Gaussian 822 and third Gaussian 823 may then be determined using the same base function to the waveform remainder When combined, the Gaussian base functions form expected characteristic fit curve 820, which approximates the bioimpedance signal waveform. The parameters that define the component base functions of expected characteristic fit curve 820, as derived from the exemplary pulse decomposition algorithm may serve to characterize each cardiac cycle in the measured bioimpedance signals.

The measured signal may then be replaced by a smooth waveform comprising the expected characteristic fit curves 820 of each cardiac cycle. This may permit the robust calculation of various points of interest such as minimum M0 621, minimum M1 622, minimum M2 623, and local curvatures at interest points. The computer parameters, relative amplitude, timing vs. ECG, and width may serve to characterize the waveform. Methods such as the disclosed exemplary pulse decomposition algorithm may be useful for detecting expected characteristics that are difficult or impossible to detect through the use of other techniques, such as inflection point determination. As illustrated in FIG. 8, peaks P1 611, P2 612, and P3 613 do not coincide with local maxima of the bioimpedance signal waveform 610, but with the peaks of the bioimpedance signal waveform's 610 component waveforms, Gaussians 821, 822 and 823.

Additional exemplary base functions may include a Generalized Extreme Value (GEV) distribution function. A GEV function may be used in conjunction with other base functions (such as Gaussians) or as the sole base function. For example, when decomposing a periodic bioimpedance signal, Gaussian base functions may be used for fitting the first P1 611 and second P2 612 peaks in the systolic part of the waveform, and a GEV function for P3 613 on the diastolic part. This choice may give a better fit for the diastolic part than using a Gaussian base function for P3 613, because GEV functions may be asymmetric while the Gaussian function is symmetric.

The parameterization of the bioimpedance signal waveform also permits the collection and comparison of additional expected characteristics, including distribution statistics of the initial parameters. For example, the distribution of P2 612 pulse timing measured on one hemisphere of a stroke patient may represent an expected characteristic, and may be compared with an expected characteristic represented by the distribution of P2 612 pulse timing derived from the second hemisphere.

In some embodiments, analyzing a signal may include fitting at least one signal to a prediction based on an extent of correlation between at least one expected characteristic and the signal. Using an analysis of expected characteristics, for example as described above, predictions may be made about future signal waveforms. That is, absent physiological changes, a bioimpedance signal waveform, for example, may be predicted to demonstrate similar expected characteristics in the future. Deviations from such a prediction may indicate physiological changes, such as a cerebrovascular event.

Expected characteristics of a bioimpedance signal, as illustrated in FIG. 6, may be analyzed to provide information for predicted changes in physiological brain conditions, for example, changes in cerebral blood flow. Expected characteristics may be continuously analyzed and compared over a period of time to provide diagnosis information. For example, bioimpedance signal waveform data may be continuously sampled to compute expected characteristics for every cardiac cycle within an uninterrupted time interval. The results from monitoring one portion of the uninterrupted time interval may be compared to the results from monitoring another portion of the uninterrupted time interval. For example, expected characteristics may be continuously monitored throughout an uninterrupted time interval during a surgery performed on a patient to diagnose any cerebral blood flow changes that occur during the surgery. The expected characteristics detected during any one time interval of arbitrary length during the surgery may be compared to expected characteristics detected at any later time interval of arbitrary length during the surgery.

Alternatively or additionally, expected characteristics may also be monitored and compared to predictions over non-continuous time periods to provide diagnosis information. For example, bioimpedance signal waveform data may be monitored during one time interval for comparison with bioimpedance signal waveform data monitored during a second time interval that does not overlap or adjoin the first time interval. For example, an expected characteristic baseline for a patient may be measured at a first time, e.g. prior to a surgery, upon admittance to a hospital, at a routine office visit, or at any other time when baseline measurement is possible. The expected characteristic baseline may then be compared to expected characteristics monitored at any later time, e.g. during a surgery, upon release from a hospital, at another routine office visit, etc.

In some embodiments, analyzing may include focusing on a time period around an expected characteristic based on an indicated physiological condition. When an analysis indicates a physiological condition, such as arterial occlusion or cerebral edema, a time period around a specific expected characteristic that may be associated with the physiological condition may be analyzed more closely. Such closer analysis may yield additional information about the physiological condition. For instance, more information about an occlusion in the MCA may be yielded from a closer analysis of the second peak P2 612.

Consistent with the present disclosure, at least one processor may be configured to output information for predicting a physiological brain condition based on the extent of at least one expected characteristic in at least one signal. As used, herein, "information for predicting a physiological brain condition," may include any type of information that may aid a physician in detecting, diagnosing, understanding, or predicting a physiological brain condition. Such information may, for example, include a direct indication of a physiological brain condition, or include information that assists in diagnosis of a physiological brain condition. Information for predicting a physiological brain condition may include specific information about the location and extent of the condition, or may include general information indicative of a change in condition. For example, as previously described, asymmetry in bioimpedance-related measurements/calculations from opposite sides of a patient's head may be information that is output for diagnosis purposes. In one embodiment, the existence of asymmetry might be the only information output. In another embodiment, a measure of asymmetry might be included in the information output. In yet another embodiment, information output may include an indicator of change in asymmetry over time.

The output information may be as simple as an indicator to a medical professional that a significant variance exists. Alternatively, or additionally, it may include informational output characterizing, for example, one or more of a magnitude of variance, a change in magnitude of variance over time, and any other data that might indicate a physiological brain condition, an extent of a physiological brain condition, or a change in the extent of a physiological brain condition.

Information for predicting a physiological brain condition may include information for diagnosing the presence of ischemic stroke. A change in artery occlusion may lead to ischemic stroke, a cerebral condition in which a portion of the brain does not receive adequate blood supply due to arterial blockage. In some embodiments, a processor may be configured to diagnose the absence of hemorrhagic stroke based on the presence of ischemic stroke. Hemorrhagic stroke is a cerebral condition in which a portion of the brain does not receive adequate blood supply due to bleeding in the brain. Outward symptoms of ischemic and hemorrhagic stroke may be similar. The presence of ischemic stroke in a subject demonstrating outward stroke symptoms may indicate the absence of hemorrhagic stroke.

Information for predicting a physiological brain condition may be based on the extent of at least one expected characteristic. As described above, a bioimpedance signal waveform obtained from the head of a subject may be indicative of cerebral blood flow. The extent of expected characteristics within a bioimpedance signal waveform, therefore, may be indicative of cerebral blood flow, and changes in the extent of expected characteristics may be indicative of changes in cerebral blood flow. Analyzing changes in cerebral blood may provide information for predicting a physiological brain condition. For example, if the height of the local maximum in each period, which corresponds to an impedance minimum, were reduced between a first and second time period, that may be indicative of a reduction in cerebral blood flow.

In some embodiments, the processor may be configured to predict a physiological brain condition based at least in part on a comparison of portions of a first signal related to a first hemisphere of a subject's brain with portions of a second signal related to a second hemisphere of a subject's brain. A comparison of portions of a first signal and portions of a second signal may include any type of analysis performed on the signals. The signals may be compared with basic arithmetic operations, such as addition, subtraction, etc. The signals may be compared in a time domain. The signals may also be compared in a frequency domain, using any suitable transform. All or part of one signal may be compared to all or part of another signal. For example, the signals may be compared in their entirety, by smaller sections, and/or by discrete points. Alternatively (or additionally), parts of one or more signals may be compared to corresponding or non-corresponding parts of one or more other signals. Further, the signals may be compared based on amplitudes, frequencies, and phase angles, as measured at time intervals of any length. The signals may also be compared based on expected characteristics of the signals.

This comparison may be a comparison between a first signal and a second signal related to differing hemisphere's of a subject's brain. Bioimpedance signals derived from opposite sides of the brain reflect the blood flow in opposite brain hemispheres. Because stroke is typically an asymmetric phenomena, comparing the expected characteristics of signals obtained from differing hemispheres may give information regarding the side of the brain affected by stroke. Bioimpedance signal waveforms such as those shown in FIG. 4 from the two hemispheres may be compared to one another to predict physiological brain conditions. In a patient exhibiting a cerebrovascular event, for example, the two bioimpedance signal waveforms will generally show a greater degree of dissimilarity than exhibited in FIG. 4 for a healthy patient.

Figure 9:
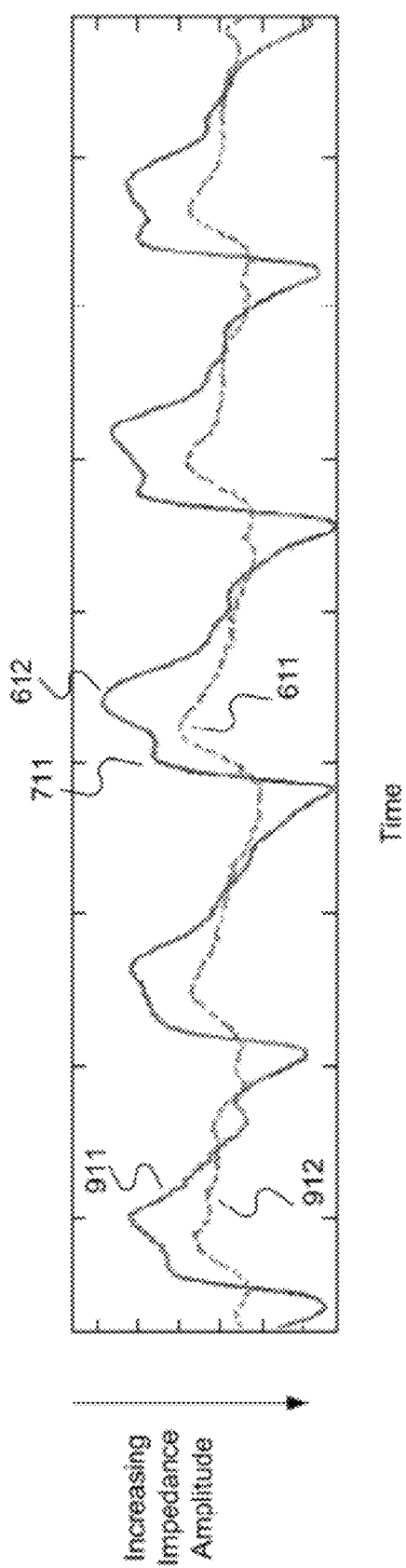
FIG. 9 provides a diagrammatic representation of a comparison between exemplary bioimpedance signals associated with different hemispheres of a subject's brain.

In the signals illustrated in FIG. 9 for example, a left hemisphere bioimpedance signal 912, illustrated by the dashed line, shows significantly reduced variations in impedance amplitudes as compared to a right hemisphere bioimpedance signal 911. Additionally, in the left hemisphere bioimpedance signal 912, peak P2 612 appears to have disappeared entirely, and the remaining peak, P1 611 exhibits a timing delay with respect to the corresponding peak of right hemisphere bioimpedance signal 911. Both reduced impedance amplitudes and timing delays may be reflective of stroke. Comparing bioimpedance signals from the left and right hemispheres may thus yield information for predicting a physiological brain condition.

According to another embodiment of the present disclosure, the processor may be further configured to calibrate features in the at least one signal with cerebral blood flow image information. Cerebral blood flow image information may include any type of image information pertaining to cerebral blood flow. Such information may include information directly constituting cerebral blood flow images, e.g. actual images, and may include information descriptive of cerebral blood flow images, e.g. measurements of blood flow obtained from images. Cerebral blood flow image information may be automatically generated by computers or the like tasked to analyze cerebral blood flow images. Such information may also be manually generated, for instance by a physician providing a diagnosis based on cerebral blood flow images. Any suitable source may provide cerebral blood flow information, such as Magnetic Resonance Imaging (MRI), transcranial doppler ultrasound (TCD), or perfusion computed tomography (PCT) and angiography (CTA).

Features of a signal received by a processor may be calibrated to correspond to cerebral blood flow information. A feature of a bioimpedance signal may be compared to and correlated with the cerebral blood information that corresponds to that feature. Such comparisons and correlations may then be used in the interpretation, quantification and modeling of data from bioimpedance signal measurements. For instance, an occlusion in a major cerebral blood vessel, such as the Middle Cerebral Artery (MCA) 240, has been shown through MRI and CTA techniques to result in delayed or reduced blood flow in this part of the brain 201. A bioimpedance signal waveform obtained from a subject experiencing such an occlusion may demonstrate signal features consistent with the occlusion. These features may be calibrated with the direct cerebral blood flow image information detailing the delayed or reduced blood flow.

The foregoing description describe some exemplary methods of receiving, correlating, and analyzing signal waveforms. Alternate embodiments, however, may utilize other methods of performing these tasks. For example, in some embodiments expected characteristics other than peaks P1 511, P2 512, and P3 513 may be used. In some embodiments, alternate pulse decomposition methods for expected characteristic detection may be used. And in some embodiments, alternate methods of expected characteristic detection may be used. Thus, it will be appreciated by those of ordinary skill that various analysis techniques exist for analyzing a signal based on the extent of an expected characteristic, and the invention in its broadest sense is not limited to any particular technique.

Figure 10:
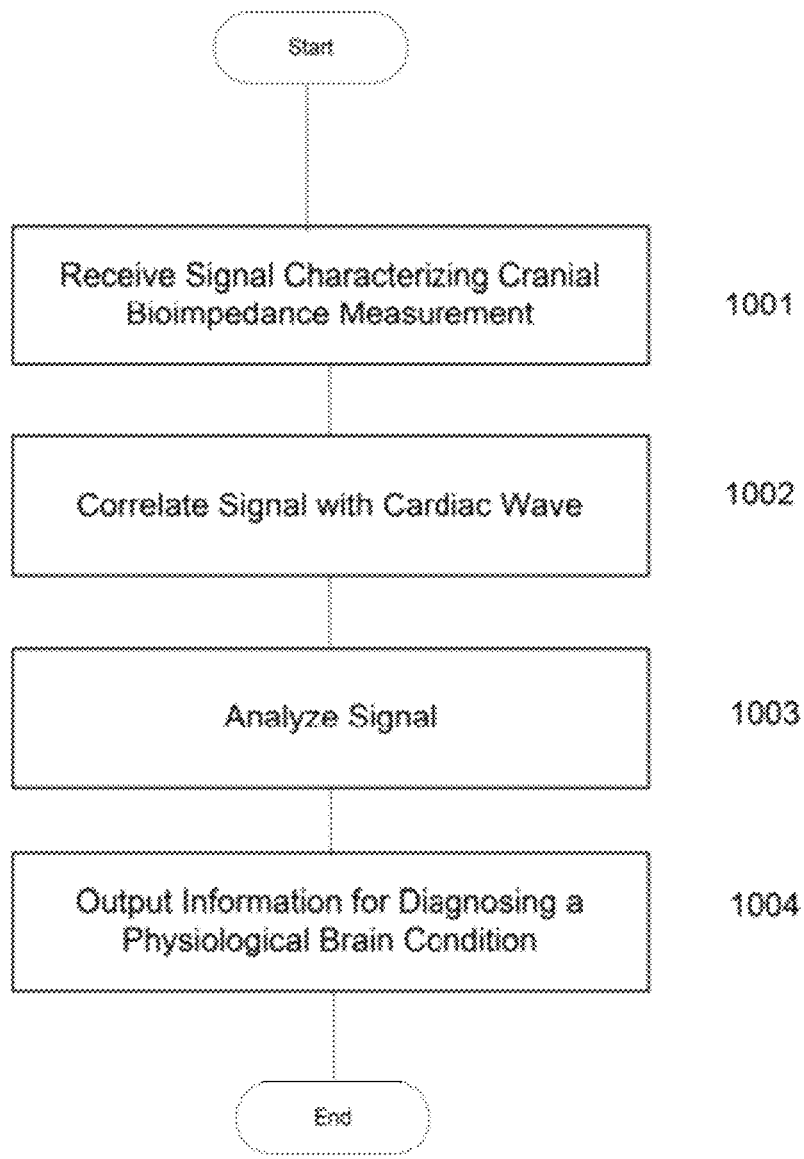
FIG. 10 is a flowchart showing the steps of an exemplary method for diagnosing a physiological brain condition.

In an embodiment consistent with the present disclosure, a method for predicting a physiological brain condition is provided. FIG. 10 is a flowchart showing the steps of an exemplary method for predicting a physiological brain condition. At step 1001, at least one signal characterizing at least one cranial bioimpedance measurement may be received. The signals may be received, for instance, by a suitably configured processor 160. At step 1002, the at least one signal may be correlated with timing of a cardiac wave. Processor 160 may be configured to perform this step.

At step 1003, the at least one signal may be analyzed to ascertain the extent of at least one characteristic in the signal. The at least one signal may be analyzed during a time period defined by the cardiac wave, and may be analyzed by a suitably configured processor 160. At step 1004, results of the analysis step 1003 may be used to output information for predicting a physiological brain condition based on the extent of the at least one expected characteristic in the at least one signal. A processor 160 may, for example, be configured to output the information. Additional methods for prediction a physiological brain condition may include any and/or all of the techniques disclosed herein.

While many of the foregoing examples were described with reference to a comparison of right and left hemispheres, it should be appreciated that measurements may be taken and compared from various locations of a subject's head, and the invention in its broadest sense does not require that comparative signals be limited only to opposing hemispheres. Similarly, while this disclosure provides examples of the analysis of bioimpedance signals, any signal that characterizes at least one cranial bioimpedance measurement may be assessed consistent with broad principles of this disclosure.

Further, the disclosure of uses of embodiments of the invention for detection, diagnosis, and monitoring of strokes and occlusions is exemplary only. In its broadest sense, the invention may be used in connection with the detection, diagnosis, and/or treatment of any physiological brain condition detectable using the principles described herein. Further, it should be appreciated that the methods and apparatus described herein to diagnose changes in artery occlusion in the brain of a subject may be generalized to diagnose changes in artery occlusion of any genesis, including stroke, vascular degeneration, etc. Alternative embodiments will become apparent to those skilled in the art to which the present invention pertains without departing from its spirit and scope. Accordingly, the scope of the present invention is defined by the appended claims rather than the foregoing description.

What is claimed is:

1. A cerebro-hemodynamic measurement apparatus, comprising:
at least one processor configured to:
receive at least one signal characterizing at least one cranial bioimpedance measurement;
correlate the at least one signal with timing of a cardiac wave;
analyze the at least one signal during a time period defined by the cardiac wave to ascertain an extent of at least one expected characteristic in the at least one signal during the time period, the analysis including:
decomposing the at least one signal into basis functions associated with parameters,
determining a distribution of at least one of the parameters, and
ascertaining the extent of the at least one expected characteristic in the at least one signal during the time period based on the distribution of the at least one of the parameters; and
output information for predicting a physiological brain condition based on the extent of the at least one expected characteristic in the at least one signal.

2. The cerebro-hemodynamic measurement apparatus of claim 1, wherein the at least one signal includes at least two bioimpedance signals, the at least two bioimpedance signals each relating to differing hemispheres of a subject's brain, and wherein the at least two bioimpedance signals are synchronized to each other.

3. The cerebro-hemodynamic measurement apparatus of claim 1, wherein the at least one expected characteristic relates to at least one of height, delay, width, and timing of a feature in a bioimpedance signal.

4. The cerebro-hemodynamic measurement apparatus of claim 1, wherein the at least one expected characteristic relates to at least one of a first peak, a second peak, and a third peak in a bioimpedance signal.

5. The cerebro-hemodynamic measurement apparatus of claim 4, wherein analyzing includes focusing on at least one time period around an expected characteristic based on an indicated physiological condition.

6. The cerebro-hemodynamic measurement apparatus of claim 1, wherein the at least one signal includes a first signal relating to a first hemisphere of a subject's brain and a second signal relating to a second hemisphere of the subject's brain, and wherein the processor is configured to predict a physiological brain condition based at least in part on a comparison of portions of the first signal with portions of the second signal.

7. The cerebro-hemodynamic measurement apparatus of claim 6, wherein the at least one processor is further configured to analyze portions of at least one of the first signal and the second signal during predetermined time periods of interest defined by the cardiac wave.

8. The cerebro-hemodynamic measurement apparatus of claim 1, wherein the at least one expected characteristic relates to at least one of a peak location, a minima location, an anticipated peak location, and an anticipated minima location.

9. The cerebro-hemodynamic measurement apparatus of claim 1, wherein correlating includes synchronizing the at least one signal with timing of a simultaneous cardiac cycle.

10. The cerebro-hemodynamic measurement apparatus of claim 1, wherein correlating includes detecting a coincidence in timing of the at least one signal with a cardiac cycle by comparing portions of the at least one signal with a known signal previously correlated to a cardiac cycle.

11. The cerebro-hemodynamic measurement apparatus of claim 1, wherein the cardiac wave includes any repeating portion of an electrocardiogram signal.

12. The cerebro-hemodynamic measurement apparatus of claim 1, wherein the cardiac wave is an electrocardiogram signal R wave.

13. The cerebro-hemodynamic measurement apparatus of claim 1, wherein the time period defined by the cardiac wave includes at least two repetitions of a cardiac cycle.

14. The cerebro-hemodynamic measurement apparatus of claim 1, wherein the basis functions include at least one of gaussian functions and generalized extreme value distribution functions.

15. A method for providing information for predicting a physiological brain condition, comprising:
    receiving at least one signal characterizing at least one cranial bioimpedance measurement obtained via at least one electrode;
    correlating, by at least one processor, the at least one signal with timing of a cardiac wave;
    analyzing, by at least one processor, the at least one signal during a time period defined by the cardiac wave to ascertain an extent of at least one expected characteristic in the at least one signal during the time period, the analysis including:
        decomposing the at least one signal into basis functions associated with parameters,
        determining a distribution of at least one of the parameters, and
        ascertaining the extent of the at least one expected characteristic in the at least one signal during the time period based on the distribution of the at least one of the parameters; and
    outputting information for predicting a physiological brain condition based on the extent of the at least one expected characteristic in the at least one signal.

16. The method of claim 15, wherein the at least one signal includes at least two signals, the at least two signals each characterizing a bioimpedance measurement relating to differing hemispheres of a subject's brain, and further comprising synchronizing the at least two signals to each other.

17. The method of claim 15, wherein the at least one expected characteristic relates to at least one of height, delay, width, and timing of a feature in a bioimpedance signal.

18. The method of claim 15, wherein the at least one expected characteristic relates to at least one of a first peak, a second peak, and a third peak in a bioimpedance curve.

19. The method of claim 15, wherein the at least one signal includes a first signal relating to a first hemisphere of a subject's brain and a second signal relating to a second hemisphere of the subject's brain, and wherein the at least one processor is configured to predict a physiological brain condition based at least in part on a comparison of portions of the first signal with portions of the second signal.

20. The method of claim 19, further comprising analyzing portions of the first signal or the second signal during predetermined time periods of interest defined by the cardiac wave.

21. The method of claim 20, wherein the at least one expected characteristic relates to at least one of a peak location, a minima location, an anticipated peak location, and an anticipated minima location.

22. The method of claim 15, wherein analyzing further comprises focusing on at least one time period around an expected characteristic based on an indicated physiological condition.

23. The method of claim 15, wherein correlating further comprises synchronizing the at least one signal with timing of a simultaneous cardiac cycle.

24. The method of claim 15, wherein correlating further comprises detecting a coincidence in timing of the at least one signal with a cardiac cycle by comparing portions of the at least one signal with a known signal previously correlated to a cardiac cycle.

25. The method of claim 15, wherein the cardiac wave includes any repeating portion of an electrocardiogram signal.

26. The method of claim 15, wherein the cardiac wave is an electrocardiogram signal R wave.

27. The method of claim 15, wherein the time period defined by the cardiac wave includes at least two repetitions of a cardiac cycle.

28. The method of claim 15, wherein the basis functions include at least one of gaussian functions and generalized extreme value distribution functions.

* * * * *